United States Patent
Yoshida et al.

(10) Patent No.: US 9,750,326 B2
(45) Date of Patent: Sep. 5, 2017

(54) TRANSPARENCY EVALUATION DEVICE, TRANSPARENCY EVALUATION METHOD AND TRANSPARENCY EVALUATION PROGRAM

(71) Applicant: FUJIFILM Corporation, Tokyo (JP)

(72) Inventors: Naoko Yoshida, Ashigara-kami-gun (JP); Ikuko Ohgaru, Ashigara-kami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 14/955,157

(22) Filed: Dec. 1, 2015

(65) Prior Publication Data

US 2016/0106198 A1 Apr. 21, 2016

Related U.S. Application Data

(63) Continuation of application No. PCT/JP2014/064746, filed on Jun. 3, 2014.

(30) Foreign Application Priority Data

Jun. 7, 2013 (JP) ................................. 2013-120650
Sep. 26, 2013 (JP) ................................. 2013-199882
Feb. 26, 2014 (JP) ................................. 2014-035658

(51) Int. Cl.
*G01B 9/00* (2006.01)
*A45D 44/00* (2006.01)
(Continued)

(52) U.S. Cl.
CPC ............ *A45D 44/00* (2013.01); *A61B 5/1032* (2013.01); *A61B 5/441* (2013.01); *G01N 21/27* (2013.01);
(Continued)

(58) Field of Classification Search
CPC ... A61B 5/441; A61B 2576/00; A61B 5/1032; A61B 5/743; A45D 2044/007;
(Continued)

(56) References Cited

FOREIGN PATENT DOCUMENTS

JP 2010-022547 A 2/2010

OTHER PUBLICATIONS

International Preliminary Report on Patentability dated Dec. 17, 2015, issued by the International Bureau in corresponding International Application No. PCT/JP2014/064746, 7 pages.

*Primary Examiner* — Tri T Ton
(74) *Attorney, Agent, or Firm* — Sughrue Mion, PLLC

(57) ABSTRACT

A transparency evaluation device includes a skin index calculation unit that calculates at least one of a luminance component in a captured image obtained by photographing a skin, a color component in the captured image, and an amount of generation of negative factors in which the luminance component or the color component in the captured image changes locally, as a first index, obtains at least one of an intensity distribution of the luminance component and an intensity distribution of the color component in the captured image, and calculates at least one of smoothness of a change in the luminance component and smoothness of a change in the color component as a second index based on the intensity distributions, and a transparency evaluation unit that evaluates transparency of the skin based on an overall index in which the first index and the second index are combined.

11 Claims, 19 Drawing Sheets

(51) Int. Cl.
  *A61B 5/103*   (2006.01)
  *G01N 21/27*   (2006.01)
  A61B 5/00      (2006.01)
  G01J 3/46      (2006.01)
  G01N 21/25     (2006.01)
  G01N 21/57     (2006.01)

(52) U.S. Cl.
  CPC ........ *A45D 2044/007* (2013.01); *A61B 5/743* (2013.01); *A61B 2576/00* (2013.01); *G01J 2003/467* (2013.01); *G01N 21/251* (2013.01); *G01N 21/57* (2013.01)

(58) Field of Classification Search
  CPC . A45D 44/00; G01J 2003/467; G01N 21/251; G01N 21/27; G01N 21/57; H01L 31/022441; H01L 31/042; H01L 31/0516; H01L 31/1804
  USPC ..... 356/237.1–237.6, 239.1–239.8, 124–127
  See application file for complete search history.

TRANSPARENCY EVALUATION DEVICE, TRANSPARENCY EVALUATION METHOD AND TRANSPARENCY EVALUATION PROGRAM

CROSS-REFERENCE TO RELATED APPLICATIONS

This application is a continuation of PCT International Application No. PCT/JP2014/064746 filed on Jun. 3, 2014, which claims priority under 35 U.S.C. §119(a) to Japanese Patent Application No. 2013-120650 filed on Jun. 7, 2013, Japanese Patent Application No. 2013-199882 filed on Sep. 26, 2013, and Japanese Patent Application No. 2014-035658 filed on Feb. 26, 2014. Each of the above applications is hereby expressly incorporated by reference, in its entirety, into the present application.

BACKGROUND OF THE INVENTION

1. Field of the Invention

The present invention relates to a transparency evaluation device, a transparency evaluation method and a transparency evaluation program, and particularly, to a transparency evaluation device, a transparency evaluation method and a transparency evaluation program in which transparency of a skin or a madeup skin is evaluated based on a captured image obtained by photographing the skin or the madeup skin.

2. Description of the Related Art

Recently, as interest in transparency of a skin has increased in the cosmetic field, various methods for evaluating transparency of skin have been proposed. However, the transparency evaluation methods greatly depend on sensory evaluation. There is a need for objective evaluation of the transparency based on a physical amount obtained by physically measuring the skin.

As methods of physically measuring a skin for transparency, for example, a method of measuring a state of the skin such as an amount of moisture, an amount of oil, a skin texture form, or the like, or a method of measuring optical properties of the skin, such as specular reflection and internal scattering has been proposed. The transparency of the skin is evaluated based on these physical amounts.

However, these measuring methods are intended to measure a local physical amount in the skin. Accordingly, a physical amount obtained by the measurement does not directly represent the transparency that is perceived when the entire skin is viewed, and it is difficult to evaluate the transparency based on this physical amount with high accuracy.

Therefore, as a method of evaluating transparency of a skin according to a perception when the entire skin is viewed, for example, evaluating transparency of a skin using an estimation equation including evaluation items such as moist sensation, textural feeling, and a perception of firmness, glossiness impression, whiteness, skin color, and color unevenness, as disclosed in JP2010-22547A, has been proposed. Since the evaluation items include items used for sensory evaluation, the transparency of the skin can be evaluated according to a perception of an appearance.

SUMMARY OF THE INVENTION

However, even when the transparency of skin is evaluated based on the evaluation items of JP2010-22547A, the evaluation is not sufficiently coincident with actual evaluation using sensory evaluation, and an evaluation result according to a perception when skin is actually viewed cannot be obtained using the evaluation items. Further, the method disclosed in JP2010-22547A is not intended to evaluate the transparency based on a measurement value obtained using a physical measurement method, and it is difficult for the method to be said to be an objective evaluation method.

Further, the above evaluation method such as the method disclosed in JP2010-22547A is intended to evaluate the transparency of a bare skin. When the transparency is similarly evaluated for a skin subjected to makeup (madeup skin), a result of the evaluation is different from that of the sensory evaluation. For example, when a foundation is applied to a face of a subject, an unnatural change may occur in the bare skin, and for example, a color of the skin is adjusted as a whole due to the foundation, and a complexion may be degraded in a portion such as a cheek portion of the face. The unnatural change occurring due to the makeup gives an impression of an impasto impression of the makeup or the like, and causes a decrease in the transparency of the madeup skin. Since such an unnatural change specific to the madeup skin is not reflected in the transparency evaluation method specific to the bare skin, such as the method disclosed in JP2010-22547A, it is difficult to evaluate the transparency of the madeup skin with high accuracy.

The present invention has been made to solve such conventional problems, and an object of the present invention is to provide a transparency evaluation device, a transparency evaluation method and a transparency evaluation program capable of objectively evaluating transparency of a skin according to a perception when the skin is viewed as a whole.

Another object of the present invention is to provide a transparency evaluation device, a transparency evaluation method and a transparency evaluation program capable of evaluating transparency of a madeup skin with high accuracy.

A transparency evaluation device according to the present invention includes: an image input unit that inputs a captured image obtained by photographing a skin of a subject; a skin index calculation unit that calculates at least one of a representative value of a luminance component in the captured image, a representative value of a color component in the captured image, and an amount of generation of negative factors in which a value of the luminance component or a value of the color component in the captured image changes locally, as a first skin evaluation index, obtains at least one of an intensity distribution of the luminance component and an intensity distribution of the color component in the captured image, and calculates at least one of smoothness of a change in the luminance component and smoothness of a change in the color component as a second skin evaluation index based on the obtained intensity distributions; an overall index calculation unit that combines a plurality of evaluation indexes including the first skin evaluation index and the second skin evaluation index calculated by the skin index calculation unit with one another to calculate an overall index for transparency of the skin; and a transparency evaluation unit that evaluates transparency of the skin of the subject based on the overall index calculated by the overall index calculation unit.

Here, it is preferable that the skin index calculation unit partitions the captured image according to the value of the luminance component and the value of the color component using a plurality of contour lines set stepwise with uniform intensity spacings in order to obtain the intensity distribution of the luminance component and the intensity distribution of the color component in the captured image.

Further, the skin index calculation unit may obtain respective spacings of a plurality of contour lines adjacent to each other, and calculate the second skin evaluation index based on a uniformity of the obtained spacings of the plurality of contour lines.

Further, the skin index calculation unit may calculate the second skin evaluation index based on the number of the plurality of contour lines partitioning the captured image.

Further, it is preferable that the skin index calculation unit sets the evaluation region for calculating the second skin evaluation index so that a linear connection from a cheek portion of the face of the subject to an outline portion of the face is made.

Further, the skin index calculation unit may calculate an average value of the luminance component in the captured image as a representative value of the luminance component, and calculate an average value of the color component in the captured image as a representative value of the color component.

Further, the skin index calculation unit may calculate the number, a total area, or an area proportion of the negative factors detected in the captured image as an amount of generation of the negative factors.

Further, the skin index calculation unit may detect a portion in which the value of the luminance component or the value of the color component in the captured image changes locally and that is larger than the negative factors as color unevenness, and calculate an amount of generation of the detected color unevenness as a third skin evaluation index, and the overall index calculation unit may combine a plurality of evaluation indexes further including the third skin evaluation index with one another to calculate the overall index.

Further, the skin index calculation unit may calculate a total area, an area proportion, or the number of instances of color unevenness detected from the captured image as an amount of generation of the color unevenness.

A transparency evaluation method according to the present invention includes inputting a captured image obtained by photographing a skin of a subject; calculating at least one of a representative value of a luminance component in the captured image, a representative value of a color component in the captured image, and an amount of generation of negative factors in which a value of the luminance component or a value of the color component in the captured image changes locally, as a first skin evaluation index, obtaining at least one of an intensity distribution of the luminance component and an intensity distribution of the color component in the captured image, and calculating at least one of smoothness of a change in the luminance component and smoothness of a change in the color component as a second skin evaluation index based on the obtained intensity distributions; combining a plurality of evaluation indexes including the first skin evaluation index and the second skin evaluation index that have been calculated with one another to calculate an overall index for transparency of the skin; and evaluating transparency of the skin of the subject based on the calculated overall index.

A transparency evaluation program according to the present invention causes a computer to execute the steps of: acquiring a captured image obtained by photographing a skin of a subject; calculating at least one of a representative value of a luminance component in the captured image, a representative value of a color component in the captured image, and an amount of generation of negative factors in which a value of the luminance component or a value of the color component in the captured image changes locally, as a first skin evaluation index, obtaining at least one of an intensity distribution of the luminance component and an intensity distribution of the color component in the captured image, and calculating at least one of smoothness of a change in the luminance component and smoothness of a change in the color component as a second skin evaluation index based on the obtained intensity distributions; combining a plurality of evaluation indexes including the first skin evaluation index and the second skin evaluation index that have been calculated with one another to calculate an overall index for transparency of the skin; and evaluating transparency of the skin of the subject based on the calculated overall index.

A transparency evaluation device according to the present invention includes an image input unit that inputs a captured image obtained by photographing a face of a subject subjected to makeup; a skin index calculation unit that calculates at least one of a representative value of a luminance component in the captured image, a representative value of a color component in the captured image, and an amount of generation of negative factors in which a value of the luminance component or a value of the color component in the captured image changes locally, as a first skin evaluation index; a makeup index calculation unit that calculates an amount of a red component due to complexion in the captured image as a first makeup evaluation index; an overall index calculation unit that combines a plurality of evaluation indexes including the first skin evaluation index and the first makeup evaluation index respectively calculated by the skin index calculation unit and the makeup index calculation unit with one another to calculate an overall index for transparency; and a transparency evaluation unit that evaluates transparency of the face of the subject subjected to makeup based on the overall index calculated by the overall index calculation unit.

Further, the makeup index calculation unit may calculate an average value of the red component in the captured image, an area of a portion in which the red component is detected in the captured image, or an area proportion of the portion in which the red component is detected in the captured image as an amount of the red component.

Further, the makeup index calculation unit may set a predetermined evaluation region in at least one of a glabella portion, a cheek portion, and a jaw portion of the face of the subject, and calculate an amount of the red component in the predetermined evaluation region.

Further, the makeup index calculation unit may detect a freckle portion in which a value of the luminance component or a value of the color component in the captured image changes locally, and calculate a color tone difference between the freckle portion and surroundings thereof as a second makeup evaluation index, and the overall index calculation unit may combine a plurality of evaluation indexes further including the second makeup evaluation index with one another to calculate the overall index.

Further, the makeup index calculation unit may detect a low luminance portion indicating a shadow generated in the face of the subject based on the value of the luminance component in the captured image as an irregularity portion, and calculate an amount of the irregularity portion as a third makeup evaluation index, and the overall index calculation unit may combine a plurality of evaluation indexes further including the third makeup evaluation index with one another to calculate the overall index.

Further, it is preferable that the makeup index calculation unit calculates an area or an area proportion of the irregularity portion in the captured image as an amount of the irregularity portion.

Further, it is preferable that the makeup index calculation unit sets a predetermined region in at least one of an eye portion and a portion extending from a nose to a mouth in the face of the subject, and calculates an amount of the irregularity portion in the predetermined region.

Further, the makeup index calculation unit may extract the luminance component derived from the makeup or the color component derived from the makeup from the captured image based on values of luminance components or values of color components different from each other derived from the skin and the makeup, extract a portion in which a value of the luminance component derived from the makeup or a value of the color component derived from the makeup changes non-uniformly, and calculate a non-uniformity of the makeup as a fourth makeup evaluation index, and the overall index calculation unit may combine a plurality of evaluation indexes further including the fourth makeup evaluation index with one another to calculate the overall index.

Further, it is preferable that the makeup index calculation unit sets a predetermined region in a cheek portion of the subject, and calculates a non-uniformity of the makeup in the predetermined region.

Further, the makeup index calculation unit may detect an intermediate gloss portion indicating shine of the face of the subject based on the intensity of the luminance component in the captured image, and calculate an amount of the intermediate gloss portion as a fifth makeup evaluation index, and the overall index calculation unit may combine a plurality of evaluation indexes further including the fifth makeup evaluation index with one another to calculate the overall index.

Further, the makeup index calculation unit may set a predetermined region in at least one of a cheekbone portion and a nose ridge portion of the face of the subject, and calculate an amount of the gloss portion in the predetermined region.

Further, the skin index calculation unit may obtain at least one of an intensity distribution of the luminance component and an intensity distribution of the color component in the captured image, and calculate at least one of smoothness of a change in the luminance component and smoothness of a change in the color component as a second skin evaluation index based on the obtained intensity distributions, and the overall index calculation unit may combine a plurality of evaluation indexes further including the second skin evaluation index with one another to calculate the overall index.

Further, the skin index calculation unit may detect a portion in which the value of the luminance component or the value of the color component in the captured image changes locally and that is larger than the negative factors as color unevenness, and calculate an amount of generation of the detected color unevenness as a third skin evaluation index, and the overall index calculation unit may combine a plurality of evaluation indexes further including the third skin evaluation index with one another to calculate the overall index.

A transparency evaluation method according to the present invention includes: inputting a captured image obtained by photographing a face of a subject subjected to makeup; calculating at least one of a representative value of a luminance component in the captured image, a representative value of a color component in the captured image, and an amount of generation of negative factors in which a value of the luminance component or a value of the color component in the captured image changes locally, as a first skin evaluation index; calculating an amount of a red component due to complexion in the captured image as a first makeup evaluation index; combining a plurality of evaluation indexes including the first skin evaluation index and the first makeup evaluation index that have been calculated with one another to calculate an overall index for transparency; and evaluating transparency of the face of the subject subjected to makeup based on the calculated overall index.

A transparency evaluation program according to the present invention causes a computer to execute the steps of: acquiring a captured image obtained by photographing a face of a subject subjected to makeup; calculating at least one of a representative value of a luminance component in the captured image, a representative value of a color component in the captured image, and an amount of generation of negative factors in which a value of the luminance component or a value of the color component in the captured image changes locally, as a first skin evaluation index; calculating an amount of a red component due to complexion in the captured image as a first makeup evaluation index; combining a plurality of evaluation indexes including the first skin evaluation index and the first makeup evaluation index that have been calculated with one another to calculate an overall index for transparency; and evaluating transparency of the face of the subject subjected to makeup based on the calculated overall index.

According to the present invention, since the transparency is evaluated based on the overall index in which the first evaluation index which is at least one of the value of the entire luminance component, the value of the entire color component and the amount of generation of the negative factors, and the second evaluation index which is at least one of the smoothness of the change in the luminance component and the smoothness of the change in the color component are combined with each other, it is possible to objectively evaluate the transparency of the skin according to a perception when the skin is viewed as a whole.

Further, according to the present invention, since the first skin evaluation index is calculated, the amount of the red component in the captured image is calculated as the first makeup evaluation index, and the transparency of the face of the subject subjected to makeup is evaluated, it is possible to evaluate the transparency of the madeup skin with high accuracy.

DESCRIPTION OF THE PREFERRED EMBODIMENTS

Hereinafter, embodiments of the present invention will be described with reference to the accompanying drawings.

Embodiment 1

Figure 1:
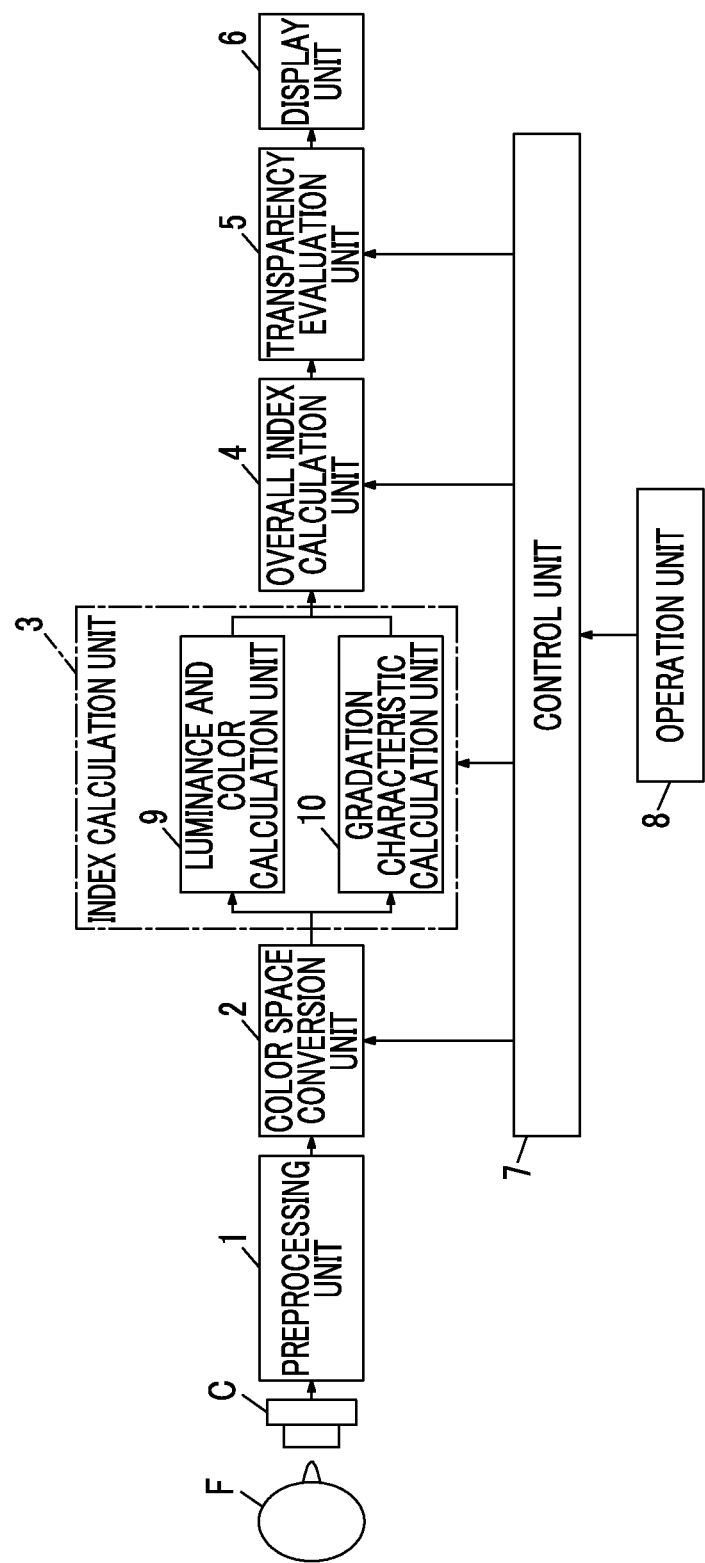
FIG. 1 is a block diagram illustrating a configuration of a transparency evaluation device according to Embodiment 1 of the present invention.

FIG. 1 illustrates a configuration of a transparency evaluation device that performs a method of evaluating transparency according to Embodiment 1 of the present invention. The transparency evaluation device is intended to evaluate transparency of a face F of a subject using a captured image obtained by photographing the face F of the subject using a camera C, and includes an image input unit (not illustrated) connected to the camera C. A preprocessing unit 1, a color space conversion unit 2, an index calculation unit 3, an overall index calculation unit 4, a transparency evaluation unit 5, and a display unit 6 are sequentially connected to the image input unit. A control unit 7 is connected to the color space conversion unit 2, the index calculation unit 3, the overall index calculation unit 4, and the transparency evaluation unit 5. An operation unit 8 is connected to the control unit 7.

The preprocessing unit 1 performs preprocessing such as light amount correction and noise removal on the captured image input from the camera C via the image input unit.

Here, the captured image input from the camera C is assumed to have an RGB color space. The camera C may be a camera capable of photographing the face F of the subject. A digital camera, a CCD camera, or the like may be used. For example, a captured image captured by a portable phone such as a smartphone may also be used.

The color space conversion unit 2 converts a color space of the captured image input from the preprocessing unit 1 to generate a color space-converted image. As the color space-converted image, for example, an image converted to an L*a*b* color space, an LCH color space, an YCC color space, or the like may be used. When the image is converted to the L*a*b* color space, a D65 light source may be used as a calculation light source. The color space conversion unit 2 divides the generated color space-converted image into a luminance component (brightness component) and a color component to generate a luminance component image and a color component image. Specifically, when the image is a color space-converted image having an L*a*b* color space, the luminance component represents an L* component, and the color component represents an a* component (complementary color component corresponding to red and green), a b* component (complementary color component corresponding to yellow and blue), a C* component (chroma component), and a Hue component (color tone component).

The index calculation unit 3 includes a luminance and color calculation unit 9 and a gradation characteristic calculation unit 10 connected to the color space conversion unit 2.

The luminance and color calculation unit 9 sets an evaluation region R1 in the face F of the subject with respect to the luminance component image and the color component image generated by the color space conversion unit 2. The evaluation region R1 may be set in, for example, the entire face F or a cheek portion. The luminance and color calculation unit 9 calculates a value of the entire luminance component in the evaluation region R1 set in the luminance component image, that is, a representative value of the luminance component in the evaluation region R1. Further, the luminance and color calculation unit 9 calculates a value of the entire color component in the evaluation region R1 set in the color component image, that is, a representative value of the color component in the evaluation region R1. The value of the entire luminance component and the value of the color component in the evaluation region R1 may be calculated from, for example, an average value of the luminance component and an average value of the color component in the evaluation region R1, respectively.

The gradation characteristic calculation unit 10 sets an evaluation region R2 in the face F of the subject with respect to the luminance generation image generated by the color space conversion unit 2. The evaluation region R2 can be set, for example, in a range from a cheek portion of the face F of the subject to an outline of the face F. The gradation characteristic calculation unit 10 obtains an intensity distribution of the luminance component in the evaluation region R2 set in the luminance component image, and calculates a gradation characteristic representing the smoothness of a change (gradation) of the luminance component over the evaluation region R2 based on the obtained intensity distribution.

The luminance and color calculation unit 9 outputs the value of the entire luminance component and the value of the entire color component in the evaluation region R1 to the overall index calculation unit 4 as a first skin evaluation index, and the gradation characteristic calculation unit 10 outputs the smoothness of the change in the luminance component over the evaluation region R2 to the overall index calculation unit 4 as a second skin evaluation index.

The overall index calculation unit 4 combines the first skin evaluation index input from the luminance and color calculation unit 9 with the second skin evaluation index input from the gradation characteristic calculation unit 10 to calculate an overall index for the transparency of the face F of the subject.

The transparency evaluation unit 5 evaluates the transparency of the face F of the subject based on the overall index calculated by the overall index calculation unit 4.

The display unit 6 includes, for example, a display device such as an LCD, and displays an evaluation result of the transparency evaluated in the transparency evaluation unit 5.

The operation unit 8 is used for an operator to perform an information input operation, and may include a keyboard, a mouse, a trackball, a touch panel, or the like.

The control unit 7 performs control of each unit of the transparency evaluation device based on various instruction signals or the like input from the operation unit 8 by the operator.

The color space conversion unit 2, the index calculation unit 3, the overall index calculation unit 4, the transparency evaluation unit 5, and the control unit 7 are configured as a CPU, and an operation program for causing the CPU to perform various processing, but may be configured as a digital circuit. Moreover, a memory can be connected to the CPU via a signal line such as a bus and, for example, the color space-converted image generated by the color space conversion unit 2, the image generated by the index calculation unit 3, and the evaluation result of the transparency calculated by the transparency evaluation unit 5 can be stored in the memory. The image and the evaluation result of the transparency stored in the memory can be displayed on the display unit 6 under the control of the control unit 7.

Further, a database in which a relationship between the sensory evaluation value calculated by performing sensory evaluation for transparency of a bare skin and the overall index has been stored in advance can be connected to the transparency evaluation unit 5. The transparency evaluation unit 5 can compare the relationship between the sensory evaluation value and the overall index read from the database with the overall index input from the overall index calculation unit 4 to evaluate the transparency of the bare skin.

Next, an operation of Embodiment 1 will be described.

First, the captured image obtained by photographing the face F of the subject using the camera C is input from the camera C to the preprocessing unit 1 of the transparency evaluation device via an image input unit (not illustrated), as illustrated in FIG. 1. The captured image is subjected to preprocessing such as light source correction and noise removal, and then output from the preprocessing unit 1 to the color space conversion unit 2. A color space of the captured image is converted into, for example, an L*a*b* color space by the color space conversion unit 2, and a color space-converted image is generated. The color space conversion unit 2 extracts a luminance component and a color component from the color space-converted image to generate a luminance component image and a color component image. For example, an L* component image can be generated as the luminance component image and a C* component image can be generated as the color component image. The generated L* component image and the generated C* component image are output from the color space conversion unit 2 to the luminance and color calculation unit 9, and the L* component image is output from the color space conversion unit 2 to the gradation characteristic calculation unit 10.

Figure 2:
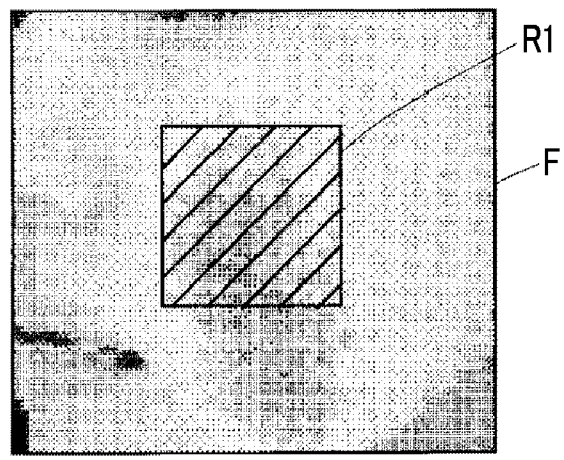
FIG. 2 is a diagram illustrating an evaluation region set in a face of a subject.

The luminance and color calculation unit 9 sets the evaluation region R1 in a cheek portion of the face F of the subject, for example, as illustrated in FIG. 2, with respect to the L* component image and the C* component image input from the color space conversion unit 2. The evaluation region R1 can be set in the L* component image and the C* component image by the operator operating the operation unit 8 through the control unit 7.

Subsequently, the luminance and color calculation unit 9 obtains an average value of the intensity of the L* component with respect to the evaluation region R1 set in the L* component image, and obtains an average value of the intensity of the C* component with respect to the evaluation region R1 set in the C* component image. Accordingly, with respect to the evaluation region R1 set in the face F of the subject, the value of the entire L* component and the value of the entire C* component can be obtained.

Generally, it is known that a skin of a person is white and has a bright color and a low chroma when the person is young, but becomes an overall yellowish and dark skin with overall low transparency due to aging. Therefore, the value of the entire L* component and the value of the entire C* component of the evaluation region R1 obtained by the luminance and color calculation unit 9 are considered as indexes indicating a change in transparency due to aging. Specifically, when the value of the entire L* component is large (bright), the transparency of the face F of the subject is experienced as being high, and when the value of the entire C* component is small, the transparency of the face F of the subject is experienced as being high. Therefore, the average value of the L* component and the average value of the C* component in the evaluation region R1 are output as the first skin evaluation index for evaluating the transparency from the luminance and color calculation unit 9 to the overall index calculation unit 4.

The average value of the L* component and the average value of the C* component in the evaluation region R1 used as the first skin evaluation index are physical amounts close to a perception when the entire face F of the subject is viewed, and the first skin evaluation index provides an objective index close to sensory evaluation for evaluation of the transparency.

Meanwhile, the gradation characteristic calculation unit 10 obtains an intensity distribution of the luminance component with respect to the predetermined evaluation region R2 of the L* component image input from the color space conversion unit 2, and calculates the gradation characteristic representing the smoothness of the change in the luminance component over the evaluation region R2 based on the obtained intensity distribution.

Figure 3A:
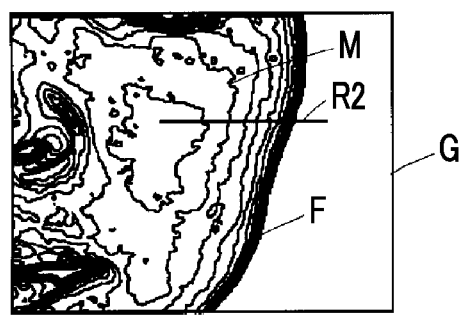
FIG. 3A is a diagram illustrating an L* component contour line distribution image of a subject with high transparency.
Figure 3B:
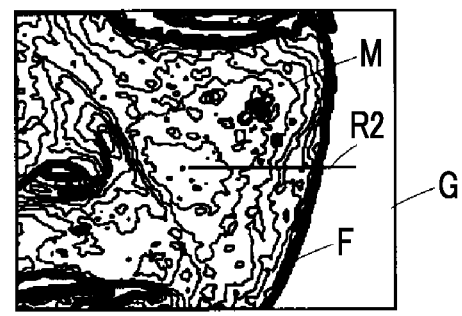
FIG. 3B is a diagram illustrating an L* component contour line distribution image of a subject with low transparency.

Specifically, the gradation characteristic calculation unit 10 sets a plurality of stepwise contour lines M stepwise with uniform intensity spacings in the face F of the subject of the L* component image, and generates an L* component contour line distribution image G obtained by partitioning the face F of the subject according to the value of the L* component using the plurality of contour lines M, as illustrated in FIGS. 3A and 3B. Here, FIG. 3A illustrates the L* component contour line distribution image G of a subject with high transparency, and FIG. 3B illustrates the L* component contour line distribution image G of a subject with low transparency. In the L* component contour line distribution image G, a region surrounded by two contour lines adjacent to each other is represented as indicating the same intensity. Thus, by partitioning the face F of the subject into the plurality of contour lines, the distribution of the L* component in the face F of the subject can be represented using the positions of the plurality of contour lines.

It is preferable for the plurality of contour lines M partitioning the face F of the subject to be set with an intensity spacing of about 1/10 with respect to an intensity range of the L* component image, or with an increment of 3 to 5 digits.

Subsequently, the gradation characteristic calculation unit 10 sets the evaluation region R2 so that a linear connection from the cheek portion of the face F of the subject to an outline portion of the face F is made with respect to the L* component contour line distribution image G. In this case, it is preferable for the evaluation region R2 to be set to pass through a portion in which the value of the L* component is largest in the cheek portion of the face F of the subject. For example, the evaluation region R2 may be set in a region linearly connecting a position at which the value of the L* component is largest in the cheek portion to the outline portion of the face F in a horizontal direction. Further, the evaluation region R2 may be set in a region linearly connecting the position at which the value of the L* component is largest in the cheek portion to the outline portion of the face F to be substantially perpendicular to and intersect the plurality of contour lines.

By the operator operating the operation unit 8, the evaluation region R2 can also be set to a predetermined region of the L* component contour line distribution image G through the control unit 7.

Figure 4A:
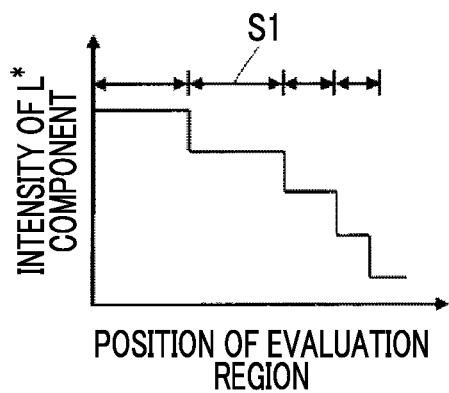
FIG. 4A is a diagram illustrating a change in an L* component in an evaluation region set in an L* component contour line distribution image of a subject with high transparency.
Figure 4B:
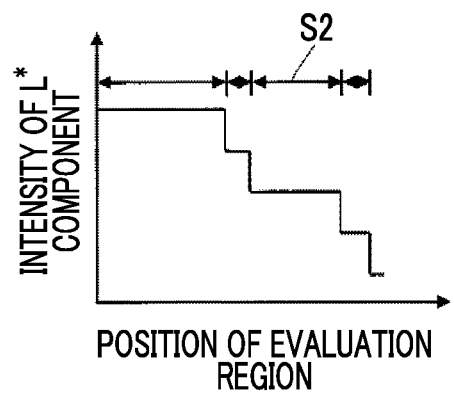
FIG. 4B is a diagram illustrating a change in an L* component in an evaluation region set in an L* component contour line distribution image of a subject with low transparency.

Thus, a change in the L* component in the evaluation region R2 set in an L* component contour line distribution image G (FIG. 3A) of a subject with high transparency is illustrated in FIG. 4A, and a change in the L* component in the evaluation region R2 set in an L* component contour line distribution image G (FIG. 3B) of a subject with low transparency is illustrated in FIG. 4B. As illustrated in FIGS. 4A and 4B, it can be seen that the change in the L* component in the evaluation region R2 of the subject with high transparency is a smooth decrease while drawing a certain curve along a curvature of the face F with respect to the change in the L* component of the subject with low transparency. Accordingly, a gradation characteristic representing smoothness of the change in the L* component may be used as a second skin evaluation index for evaluating the transparency.

For example, respective spacings of the plurality of contour lines M adjacent to each other in the evaluation region R2 may be obtained, and the gradation characteristic of the L* component can be calculated based on a uniformity of the obtained spacings of the plurality of contour lines M. That is, as illustrated in FIGS. 4A and 4B, a difference between spacing S1 of the plurality of contour lines M in the evaluation region R2 of the subject with high transparency and spacing S2 of the plurality of contour lines M in the evaluation region R2 of the subject with low transparency is small. This becomes one factor for improving the smoothness of the change in the L* component. Accordingly, by obtaining the differences between the spacings S1 and the spacings S2 by calculating respective standard deviations or the like, it is possible to quantify the gradation characteristic of the L* component. The spacings S1 and S2 of the plurality of contour lines M may be obtained from, for example, the number of pixels in the L* component contour line distribution image G, and the uniformity of spacings of the plurality of contour lines M may be calculated by obtaining a difference between the obtained number of pixels.

Further, the gradation characteristic of the L* component may also be calculated based on the number of the plurality of contour lines M partitioning the evaluation region R2. As illustrated in FIGS. 3A and 3B, the subject with high transparency has a larger number of contour lines M partitioning the evaluation region R2 than a subject with low transparency, which is a factor for improving smoothness in a change in the L* component. Therefore, by obtaining the number of the plurality of contour lines M partitioning the evaluation region R2, it is possible to quantify a gradation characteristic of the L* component.

The gradation characteristic of the L* component obtained in this manner is output as the second skin evaluation index from the gradation characteristic calculation unit 10 to the overall index calculation unit 4.

The second skin evaluation index is intended to evaluate the transparency based on a change in the luminance of the face F of the subject, unlike the first skin evaluation index for evaluating the transparency based on the entire luminance of the face F of the subject, and can be used to evaluate the transparency from a different viewpoint from the first skin evaluation index. Further, the gradation characteristic of the L* component used as the second skin evaluation index is a physical amount close to the perception when the entire face F of the subject is viewed, similar to the first skin evaluation index, and the second skin evaluation index provides an objective index close to sensory evaluation for evaluation of the transparency.

Thus, the value of the entire L* component and the value of the entire C* component in the evaluation region R1 obtained by the luminance and color calculation unit 9 are input as the first skin evaluation index to the overall index calculation unit 4, and the gradation characteristic of the L* component in the evaluation region R2 obtained by the gradation characteristic calculation unit 10 is input as the second skin evaluation index to the overall index calculation unit 4.

The overall index calculation unit 4 performs linear summation on the first skin evaluation index and the second skin evaluation index that have been input, that is, the value of the entire L* component of the evaluation region R1, the value of the entire C* component of the evaluation region R1, and the gradation characteristic of the L* component of the evaluation region R2 using, for example, a multiple regression equation obtained by performing sensory evaluation in advance, to thereby combine the values and the gradation characteristic with one another and calculate the overall index for determining the evaluation of the transparency for the face F of the subject. The value of the calculated overall index is output from the overall index calculation unit 4 to the transparency evaluation unit 5.

The transparency evaluation unit 5 evaluates the transparency of the face F of the subject based on the overall index calculated by the overall index calculation unit 4, and a result of the evaluation is displayed on the display unit 6.

According to this embodiment, since the transparency is objectively evaluated according to a perception when the face F of the subject is viewed as a whole based on the overall index in which the first skin evaluation index and the second skin evaluation index are combined with each other, it is possible to obtain an evaluation result sufficiently coincident with the evaluation of the transparency through the sensory evaluation. The second skin evaluation index for evaluating the transparency based on the change in the luminance component is a new evaluation index that is not in the related art. By evaluating the transparency based on the overall index in which the second skin evaluation index is added, it is possible to achieve an evaluation result close to the evaluation of the transparency through the sensory evaluation.

An example of the embodiment in which the transparency was actually evaluated using the above-described transparency evaluation method will be described.

In this embodiment, the transparency was evaluated using the transparency evaluation method of Embodiment 1 and sensory evaluation for transparency was performed on 8 subjects in their 40s. Here, in the transparency evaluation method of Embodiment 1, the average value of the L* component in the evaluation region R1, the average value of the C* component in the evaluation region R1, and the uniformity of spacings of a plurality of contour lines partitioning the evaluation region R2 were calculated for each subject, and combined with each other to obtain an overall index for transparency. The uniformity of spacings of the plurality of contour lines M was obtained by obtaining spacings between the plurality of contour lines M based on the number of pixels in the image and calculating differences between the numbers of pixels representing spacings of the plurality of contour lines M. A numerical value decreases as the spacings of the contour lines become more uniform.

Figure 5:
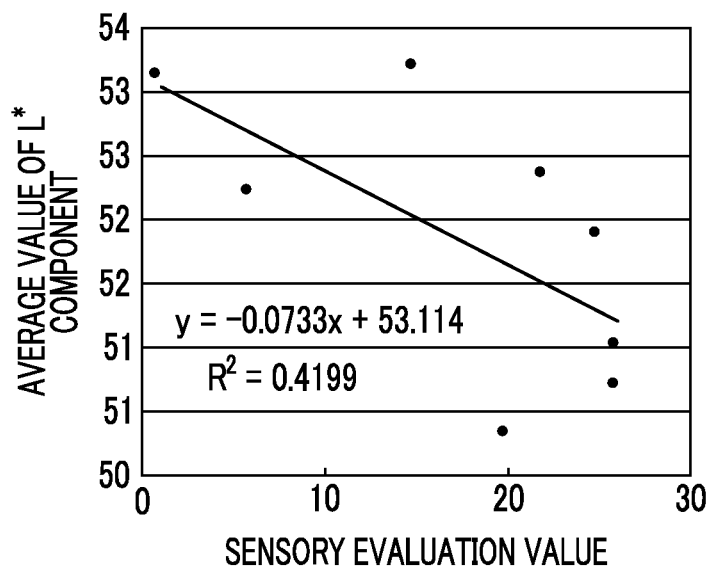
FIG. 5 is a diagram illustrating an obtained correlation between an average value of an L* component and a sensory evaluation value.
Figure 6:
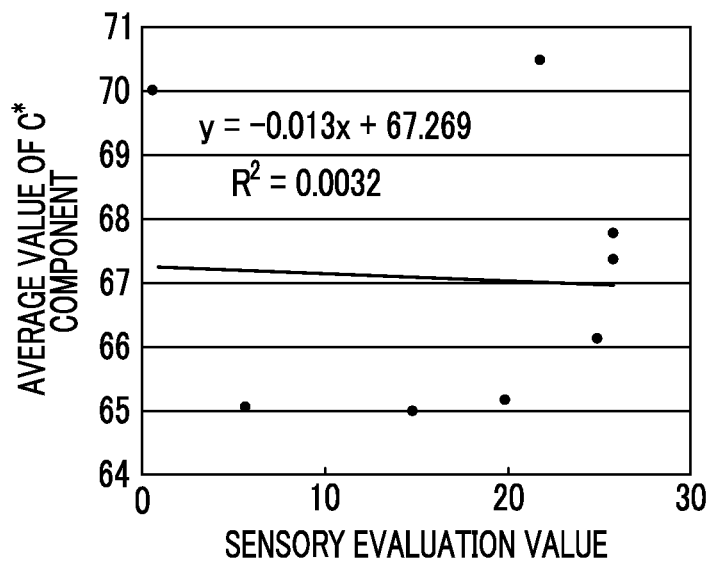
FIG. 6 is a diagram illustrating an obtained correlation between an average value of a C* component and the sensory evaluation value.
Figure 7:
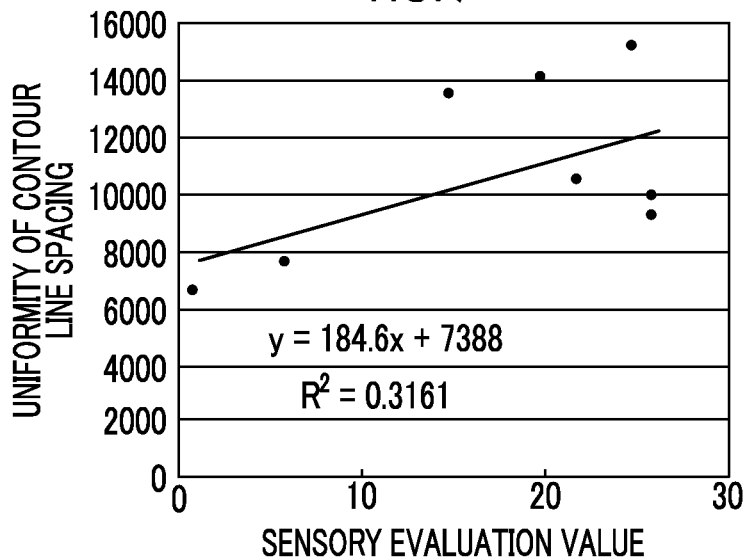
FIG. 7 is a diagram illustrating an obtained correlation between a uniformity of spacings of contour lines and the sensory evaluation value.

FIG. 5 illustrates a graph obtained by plotting the average value of the L* component in the evaluation region R1 with respect to the sensory evaluation value, FIG. 6 illustrates a graph obtained by plotting the average value of the C* component in the evaluation region R1 with respect to the sensory evaluation value, and FIG. 7 illustrates a graph obtained by plotting the uniformity of spacings of a plurality of contour lines partitioning the evaluation region R2 with respect to the sensory evaluation value. Here, for the sensory evaluation value, the transparency is evaluated in 30 steps through sensory evaluation. No transparency is evaluated when the value becomes closer to 30.

When a correlation between the average value of the L* component and the sensory evaluation value was obtained based on FIG. 5, a correlation coefficient $R^2$ was 0.42. Further, when a correlation between the average value of the C* component and the sensory evaluation value is obtained based on FIG. 6, the correlation coefficient $R^2$ was 0.0032. Moreover, when a correlation between the uniformity of spacings of the contour lines and the sensory evaluation value is obtained based on FIG. 7, the correlation coefficient $R^2$ was 0.32. Subsequently, in FIGS. 5 to 7, when multiple regression analysis of the average value L of the L* component, the average value C of the C* component, and the uniformity K of the contour line spacings is performed, a multiple regression equation of sensory evaluation value S (overall index value)=177.1−410.9×L+83.5×C−33.7×K was obtained.

Figure 8:
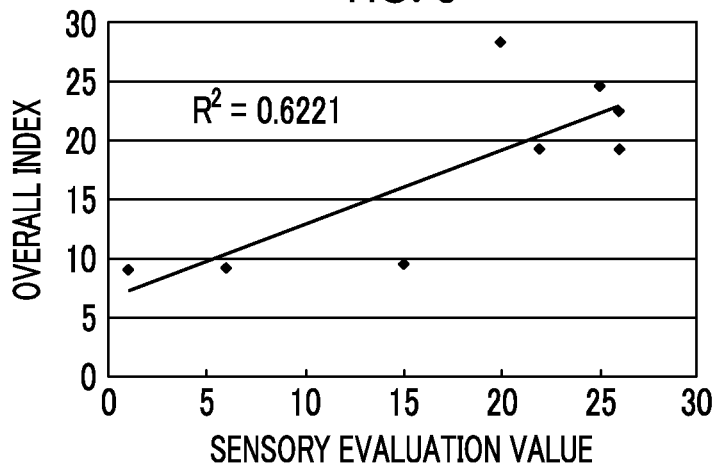
FIG. 8 is a diagram illustrating an obtained correlation between an overall index and the sensory evaluation value used in Embodiment 1.

Therefore, in the evaluation method of Embodiment 1, the average value L of the L* component, the average value C of the C* component, and the uniformity K of the contour line spacings are applied to the multiple regression equation so as to combine the values with one another and determine the overall index for transparency. A graph obtained by plotting the overall index with respect to the sensory evaluation value is illustrated in FIG. 8. When a correlation between the overall index value and the sensory evaluation value is obtained based on FIG. 8, the correlation coefficient $R^2$ was 0.62.

Thus, it can be seen that the overall index exhibits sufficiently high correlation with the sensory evaluation value, and the transparency can be evaluated with high accuracy by newly adding the uniformity of the contour line spacings, as well as the average value of the L* component and the average value of the C* component, as indexes for evaluating the transparency.

In Embodiment 1, while the luminance and color calculation unit 9 obtains the value of the entire L* component and the value of the entire C* component with respect to the evaluation region R1 set in the face F of the subject and uses the values as the first skin evaluation index, the luminance and color calculation unit 9 may obtain at least one of the value of the entire luminance component and the value of the entire color component and use the value as the first skin evaluation index, and the present invention is not limited thereto. For example, only the value of the entire L* component or only the value of the entire C* component can be used as the first skin evaluation index. Further, in the evaluation region R1, the average value of the a* component, the average value of the b* component, and the average value of the Hue component are obtained, and at least one of the average values may be used as a value of the entire color component, that is, the first skin evaluation index.

Further, while the gradation characteristic calculation unit 10 obtains the smoothness of the change in the L* component over the evaluation region R2 and uses the smoothness as the second skin evaluation index in Embodiment 1, the gradation characteristic calculation unit 10 may obtain the intensity distribution of the luminance component and the intensity distribution of the color component in the evaluation region R2 and calculate, as a second skin evaluation index, at least one of the smoothness of the change in the luminance component and the smoothness of the change in the color component over the evaluation region R2 based on the obtained intensity distributions. The present invention is not limited thereto. For example, only the smoothness of the change in the C* component over the evaluation region R2 can be calculated as the second skin evaluation index, or the smoothness of the change in the L* component and the smoothness of the change in the C* component over the evaluation region R2 can be calculated as the second skin evaluation index. Further, smoothness of a change in the a* component, smoothness of a change in the b* component, and smoothness of a change in the Hue component over the evaluation region R2 can also be calculated as the second skin evaluation index.

Further, it is not necessary to calculate the overall index using all of the first skin evaluation index obtained by the luminance and color calculation unit 9 and the second skin evaluation index obtained by the gradation characteristic calculation unit 10. For example, the control unit 7 can select the indexes calculated by the luminance and color calculation unit 9 and the gradation characteristic calculation unit 10 according to the age of the subject or the like such that desired evaluation accuracy is maintained.

Further, while the camera C photographing the face F of the subject is connected to the transparency evaluation device and the captured image is input to the preprocessing unit 1 in Embodiment 1, the transparency evaluation device may include a built-in camera. Accordingly, for example, the transparency evaluation device can be included in a device having a camera mounted thereon, such as a digital camera, a portable phone (for example, a smartphone), or a tablet.

Further, the transparency evaluation device may also input the captured images to the preprocessing unit 1 over a network. For example, the transparency evaluation device may be connected to a computer in which the captured image has been stored, over a network, evaluate the transparency of the skin based on the captured image input from the computer, and store a result of the evaluation in a server or the like. Accordingly, the user can view the evaluation result of the transparency or obtain the evaluation result of the transparency from the server over the network by accessing the server.

Embodiment 2

Figure 9:
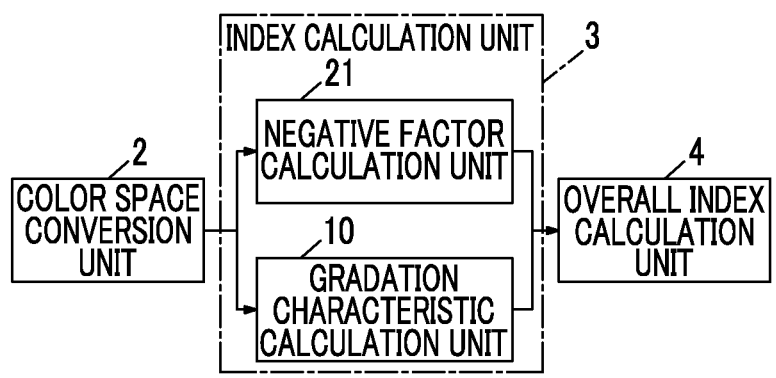
FIG. 9 is a block diagram illustrating a configuration of an index calculation unit of a transparency evaluation device according to Embodiment 2.

FIG. 9 illustrates a configuration of a transparency evaluation device that performs a method of evaluating transparency according to Embodiment 2. In this transparency evaluation device, a negative factor calculation unit 21 is arranged in the index calculation unit 3 in place of the luminance and color calculation unit 9, and is connected to the color space conversion unit 2 and the overall index calculation unit 4 in the transparency evaluation device of Embodiment 1 illustrated in FIG. 1.

The negative factor calculation unit 21 sets an evaluation region R3 in the face F of the subject of the luminance component image or the color component image generated by the color space conversion unit 2, and detects negative factors such as freckles and pores in which the value of the luminance component or the value of the color component changes locally in the set evaluation region R3. Here, the evaluation region R3 may be set in, for example, the entire face F or a cheek portion of the subject. Subsequently, the negative factor calculation unit 21 obtains an amount of generation of the negative factors in the evaluation region R3 based on a result of the detection.

A negative factor can be specified by generating a Dog image and extracting freckles and pores from the Dog image. For example, when the L* component image is input from the color space conversion unit 2 to the negative factor calculation unit 21, a Dog image with a different Gaussian size (Difference of Gaussian image) is generated from the L* component image. In general, a freckle has a size of 2 mm to 10 mm and a frequency of 0.05 cycle/mm to 0.25 cycle/mm, and a pore has a size of 0.5 mm to 2 mm and a frequency of 0.25 cycle/mm to 1.0 cycle/mm. Thus, the negative factor calculation unit 21 performs Dog image processing so that a component having a frequency band of freckles and pores is extracted. Further, at the time of this Dog image processing, a shape of each component is calculated from the binarized image subjected to threshold processing, and a portion which has a round shape and in which a degree of circularity $(4\pi \times \text{area})/\text{circumference length}^2$ is 0.4 to 1.0 and, preferably, 0.6 to 1.0, and a circumference length is 0.5 mm to 10 mm is detected as a negative factor. That is, a negative factor is detected by performing Dog image processing based on the frequency band and the size.

The Dog image may be generated using the color component image, such as an a* component image and a b* component image, as well as the L* component image, so as to detect a negative factor in the same manner as described above. Further, the Dog image may be generated using a B channel of an RGB color space and a negative factor may be detected from the Dog image.

Further, a negative factor may also be detected, for example, by extracting a component having an intensity equal to or smaller than a predetermined threshold value from the L* component image and performing primary component analysis and independent component analysis on the extracted component, instead of generating the Dog image.

The negative factor calculation unit 21 calculates an amount of generation of negative factors such as the number, the total area, and the area proportion of the negative factors based on a result of detecting the negative factors in the evaluation region R3. Here, the total area of the negative factors can be calculated from the number of pixels constituting the negative factors in the image. Negative factors are generated with aging, and when the amount of generation thereof is small, the transparency of the face F of the subject is experienced as being high. For freckles among the negative factors, a concentration of the color greatly affects the transparency, and accordingly, a concentration of the freckles with respect to the surrounding skin can be calculated as an amount of generation of negative factors. The concentration of the freckles can be obtained, for example, by obtaining an average value of the color component of the entire evaluation region R3, obtaining an average value of the color component of the freckle portion detected in the evaluation region R3, and calculating a difference (color difference) between the average value of the color component of the entire evaluation region R3 and the average value of the color component of the freckle portion.

Thus, the calculated amount of generation of the negative factors in the evaluation region R3 is output as the first skin evaluation index from the negative factor calculation unit 21 to the overall index calculation unit 4.

The amount of generation of the negative factors in the evaluation region R3 used as the first skin evaluation index is a physical amount close to the perception when the entire face F of the subject is viewed, and the first skin evaluation index provides an objective index close to the sensory evaluation for evaluation of transparency.

The number, the total area, and the area proportion of negative factors are input as the first skin evaluation index from the negative factor calculation unit 21 to the overall index calculation unit 4, and smoothness of the change in the L* component is input as the second skin evaluation index from the gradation characteristic calculation unit 10 to the overall index calculation unit 4. The overall index calculation unit 4 combines the number of the negative factors, the total area of the negative factors, the area proportion of the negative factors, and the smoothness of the change in the L* component, which have been input, with one another using a multiple regression equation, thereby calculating the overall index for determining the evaluation of the transparency of the face F of the subject.

The transparency evaluation unit 5 evaluates the transparency of the face F of the subject based on the overall index calculated by the overall index calculation unit 4. A result of the evaluation is displayed on the display unit 6.

According to this embodiment, since the transparency is objectively evaluated according to a perception when the face F of the subject is viewed as a whole based on the overall index in which the first skin evaluation index and the second skin evaluation index are combined with each other, it is possible to obtain an evaluation result sufficiently coincident with the evaluation of the transparency through the sensory evaluation.

Figure 10:
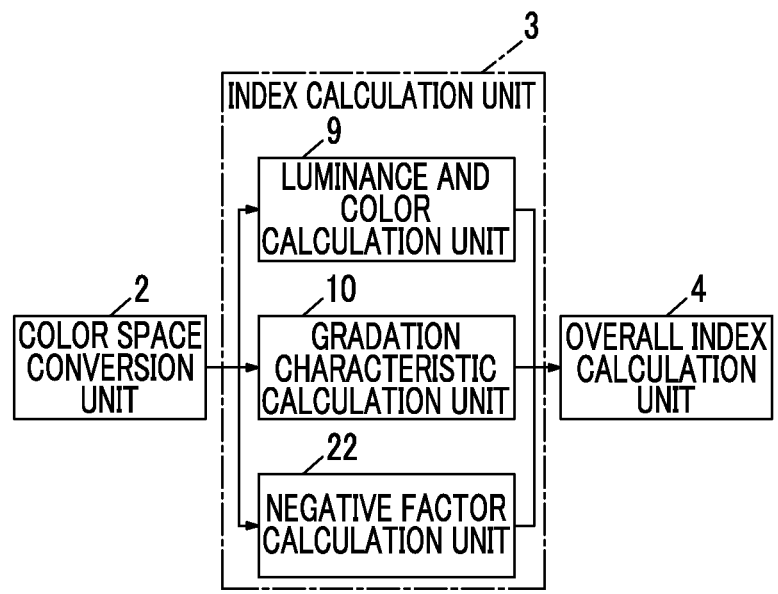
FIG. 10 is a block diagram illustrating a configuration of an index calculation unit of a transparency evaluation device according to a modification example of Embodiment 2.

As illustrated in FIG. 10, in the transparency evaluation device of Embodiment 1 illustrated in FIG. 1, a negative factor calculation unit 22 is newly provided in the index calculation unit 3, and connected to the color space conversion unit 2 and the overall index calculation unit 4, thereby forming a transparency evaluation device.

Similarly, in the negative factor calculation unit 22, the number of negative factors, a total area, and an area proportion are calculated as the first skin evaluation index, and the first skin evaluation index is output to the overall index calculation unit 4.

In the overall index calculation unit 4, the value of the entire L* component and the value of the entire C* component in the evaluation region R1 are input from the luminance and color calculation unit 9, the smoothness of the change in the L* component in the evaluation region R2 is input from the gradation characteristic calculation unit 10, and the number, the total area, and the area proportion of negative factors are input from the negative factor calculation unit 22. The overall index calculation unit 4 combines the value of the entire L* component of the evaluation region R1, the value of the entire C* component of evaluation region R1, the smoothness of the change in the L* component of the evaluation region R2, the number of negative factors, the total area of the negative factors, and the area proportion of the negative factors, which have been input, with one another using a multiple regression equation or the like, thereby calculating the overall index for determining the evaluation of the transparency of the face F of the subject.

The transparency evaluation unit 5 evaluates the transparency of the face F of the subject based on the overall index calculated by the overall index calculation unit 4. A result of the evaluation is displayed on the display unit 6. Thus, it is possible to evaluate the transparency with high accuracy by evaluating the transparency based on a larger number of indices having different properties.

Embodiment 3

In the transparency evaluation device according to Embodiments 1 and 2, a color unevenness calculation unit that detects color unevenness of the face F of the subject and calculates an amount of generation thereof can be newly provided in the index calculation unit 3 to configure the transparency evaluation device.

Figure 11:
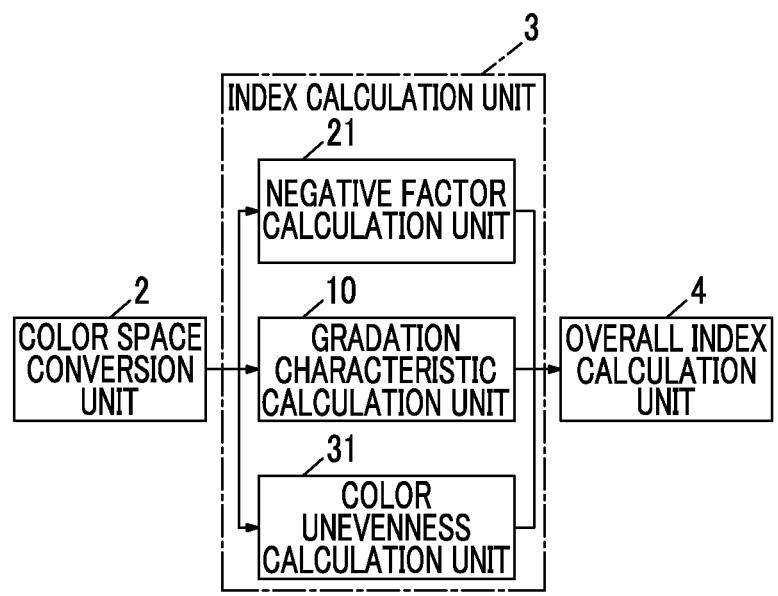
FIG. 11 is a block diagram illustrating a configuration of an index calculation unit of a transparency evaluation device according to Embodiment 3.

For example, as illustrated in FIG. 11, a color unevenness calculation unit 31 may be newly provided in the index calculation unit 3 and connected to the color space conversion unit 2 and the overall index calculation unit 4 in the transparency evaluation device according to Embodiment 2 illustrated in FIG. 9.

The color unevenness calculation unit 31 sets an evaluation region R4 in the face F of the subject of the luminance component image or the color component image generated by the color space conversion unit 2, and detects a portion in which the value of the luminance component or the value of the color component in the set evaluation region R4 changes locally and that is larger than the negative factors, as color unevenness. Here, the evaluation region R4 may be set in the entire face F, a cheek portion, or the like of the subject. Subsequently, the color unevenness calculation unit 31 obtains an amount of generation of the color unevenness in the evaluation region R4 based on a result of the detection.

A Dog image may be generated and the color unevenness may be extracted from the Dog image, similar to the negative factors. In general, the color unevenness has a size equal to or greater than about 10 mm and a frequency equal to or higher than 0.05 cycle/mm. Therefore, the Dog image is generated such that a portion having a frequency equal to or higher than 0.05 cycle/mm is extracted from the L* component image input from the color space conversion unit 2. Further, at the time of this Dog image processing, a shape of each component is calculated from the binarized image subjected to threshold processing, and a portion which has a round shape and in which a degree of circularity ($4\pi \times$ area)/circumference length$^2$ is 0.4 to 1.0 and, preferably, 0.6 to 1.0, and a circumference length is equal to or greater than about 10 mm is detected as color unevenness. That is, the color unevenness is detected by performing Dog image processing based on the frequency band and the size.

The Dog image may be generated using the color component image, such as the a* component image and the b* component image, as well as the L* component image, and the color unevenness may be detected in the same manner as described above. Further, the Dog image may be generated using a B channel of an RGB color space, and the color unevenness may be detected from the Dog image.

The color unevenness calculation unit 31 calculates the amount of generation of the color unevenness such as the total area, the area proportion, and the number of instances of color unevenness based on a result of detecting the color unevenness in the evaluation region R4. Here, the total area of the color unevenness can be calculated from, for example, the number of pixels constituting the color unevenness in the image. This color unevenness is generated with aging, and when the amount of generation thereof is small, the transparency of the face F of the subject is experienced as being high. Therefore, the color unevenness calculation unit 31 outputs the amount of generation of the color unevenness in the evaluation region R4 as a third skin evaluation index to the overall index calculation unit 4.

The amount of generation of the color unevenness in the evaluation region R4 used as the third skin evaluation index is a physical amount close to the perception when the entire face F of the subject is viewed, and the third skin evaluation index provides an objective index close to the sensory evaluation for evaluation of transparency.

The number, the total area, and the area proportion of negative factors are input as the first skin evaluation index from the negative factor calculation unit 21 to the overall index calculation unit 4, the smoothness of change in the L* component is input as the second skin evaluation index from the gradation characteristic calculation unit 10 to the overall index calculation unit 4, and a total area and an area proportion of the color unevenness are input as the third skin evaluation index from the color unevenness calculation unit 31 to the overall index calculation unit 4. The overall index calculation unit 4 combines the number of the negative factors, the total area of the negative factors, the area proportion of the negative factors, the smoothness of the change in the L* component, the total area of the color unevenness, and the area proportion of the color unevenness, which have been input, with one another using a multiple regression equation, thereby calculating the overall index for determining the evaluation of the transparency of the face F of the subject.

The transparency evaluation unit 5 evaluates the transparency of the face F of the subject based on the overall index calculated by the overall index calculation unit 4. A result of the evaluation is displayed on the display unit 6.

According to this embodiment, since the transparency is objectively evaluated according to a perception when the face F of the subject is viewed as a whole based on the overall index in which the first skin evaluation index, the second skin evaluation index, and the third skin evaluation index are combined with one another, it is possible to obtain an evaluation result sufficiently coincident with the evaluation of the transparency through the sensory evaluation.

An example of an embodiment in which the transparency was actually evaluated using the transparency evaluation method according to Embodiment 3 described above is shown.

In this embodiment, the transparency was evaluated and sensory evaluation for transparency was performed on 8 subjects in their 40s using the transparency evaluation method of Embodiment 3. Here, in the transparency evaluation method of Embodiment 3, for each subject, the total area of the freckles in the evaluation region R3, the total area of the pores in the evaluation region R3, the uniformity of spacings of the plurality of contour lines partitioning the evaluation region R2, and the total area of the color unevenness in the evaluation region R4 are calculated and combined with one another to obtain an overall index for transparency. The total area of the freckles, the total area of the pores, and the total area of the color unevenness are calculated from the number of pixels constituting the freckles, the pores, and the color unevenness.

Figure 12:
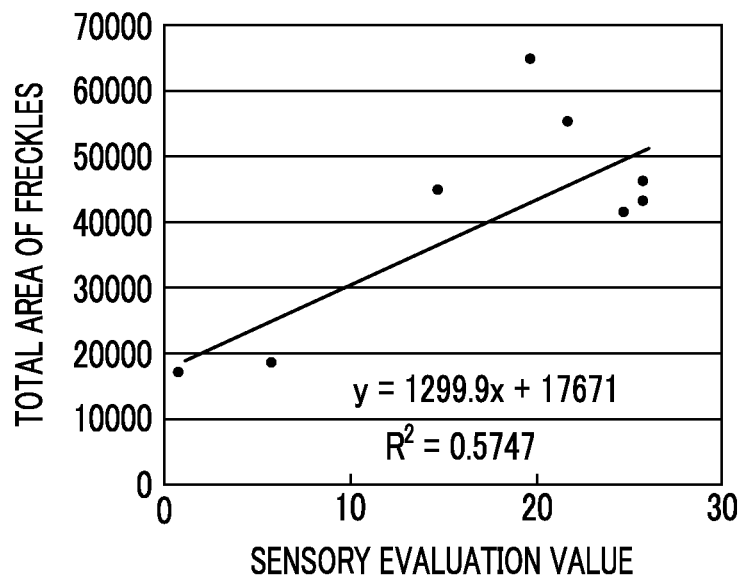
FIG. 12 is a diagram illustrating an obtained correlation between a total area of freckles and a sensory evaluation value.
Figure 13:
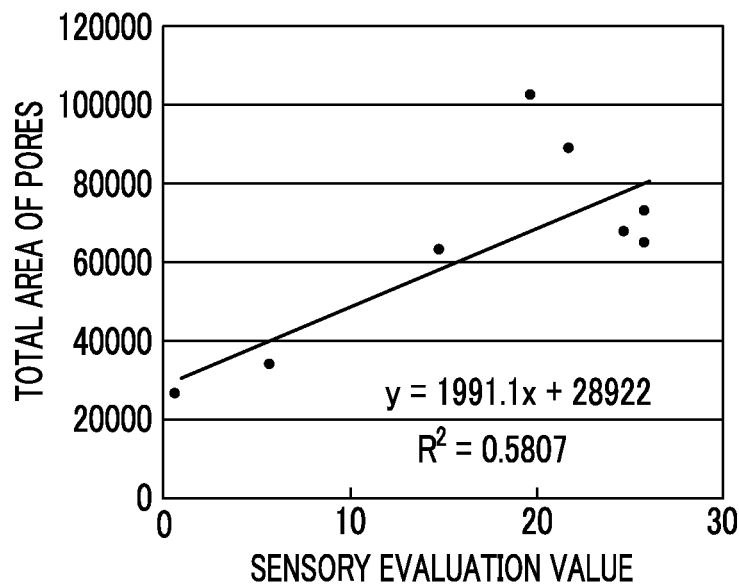
FIG. 13 is a diagram illustrating an obtained correlation between a total area of pores and a sensory evaluation value.
Figure 14:
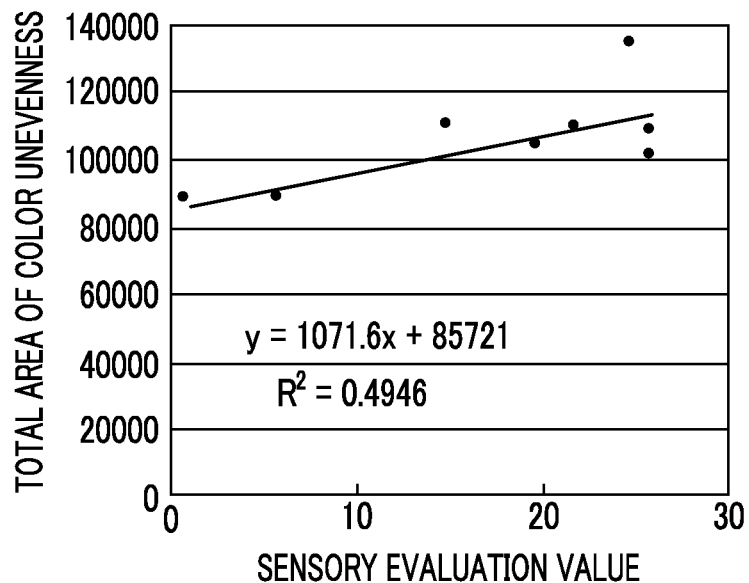
FIG. 14 is a diagram illustrating an obtained correlation between a total area of color unevenness and a sensory evaluation value.

FIG. 12 illustrates a graph obtained by plotting a total area of the freckles in the evaluation region R3 with respect to the sensory evaluation value, FIG. 13 illustrates a graph obtained by plotting the total area of pores in the evaluation region R3 with respect to the sensory evaluation value, and FIG. 14 illustrates a graph obtained by plotting a total area of color unevenness in the evaluation region R4 with respect to the sensory evaluation value.

When a correlation between the total area of the freckles and the sensory evaluation value is obtained based on FIG. 12, the correlation coefficient $R^2$ was 0.57. When a correlation between the total area of the pores and the sensory evaluation value is obtained based on FIG. 13, the correlation coefficient $R^2$ was 0.58. Further, when a correlation between the total area of the color unevenness and the sensory evaluation value is obtained based on FIG. 14, the correlation coefficient $R^2$ was 0.49. Further, as shown above, the correlation coefficient $R^2$ between the uniformity of spacings of the contour lines and the sensory evaluation value obtained based on FIG. 7 was 0.32.

Subsequently, in FIGS. 12 to 14 and 7, when the total area F of the freckles, the total area P of the pores, the total area I of the color unevenness, and the uniformity K of the spacings of the contour lines were subjected to multiple regression analysis, a multiple regression equation of sensory evaluation value S (overall index value)=−79.67−112.26×F+153.72×P+134.45×I+41.98×K was obtained.

Figure 15:
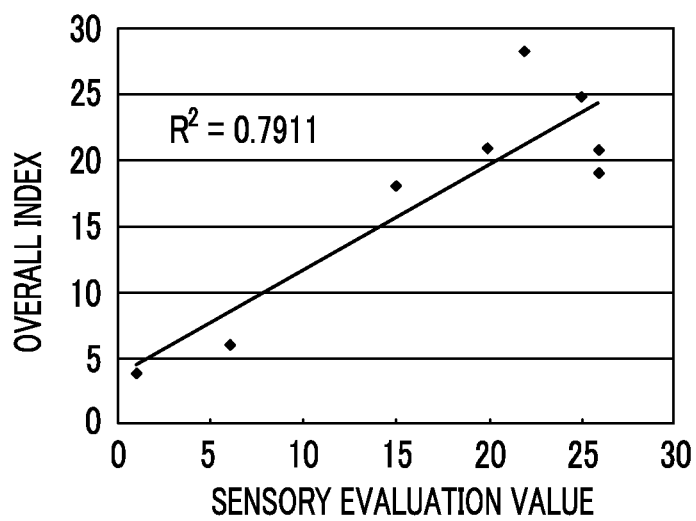
FIG. 15 is a diagram of an obtained correlation between an overall index and a sensory evaluation value used in Embodiment 3.

Therefore, in the evaluation method of Embodiment 3, the total area F of the freckles, the total area P of the pores, the total area I of the color unevenness, and the uniformity K of the spacings of the contour lines are applied to the multiple regression equation to be combined with one another, thereby obtaining an overall index for transparency. A graph obtained by plotting this overall index with respect to the sensory evaluation value is illustrated in FIG. 15. When the correlation between the overall index and the sensory evaluation value was obtained based on FIG. 15, the correlation coefficient $R^2$ was 0.79.

Thus, it can be seen that the overall index indicates a sufficiently higher correlation with the sensory evaluation value, and the transparency can be evaluated with high accuracy by combining the total area F of the freckles, the total area P of the pores, the total area I of the color unevenness, and the uniformity K of the contour line spacings with one another.

Embodiment 4

Figure 16:
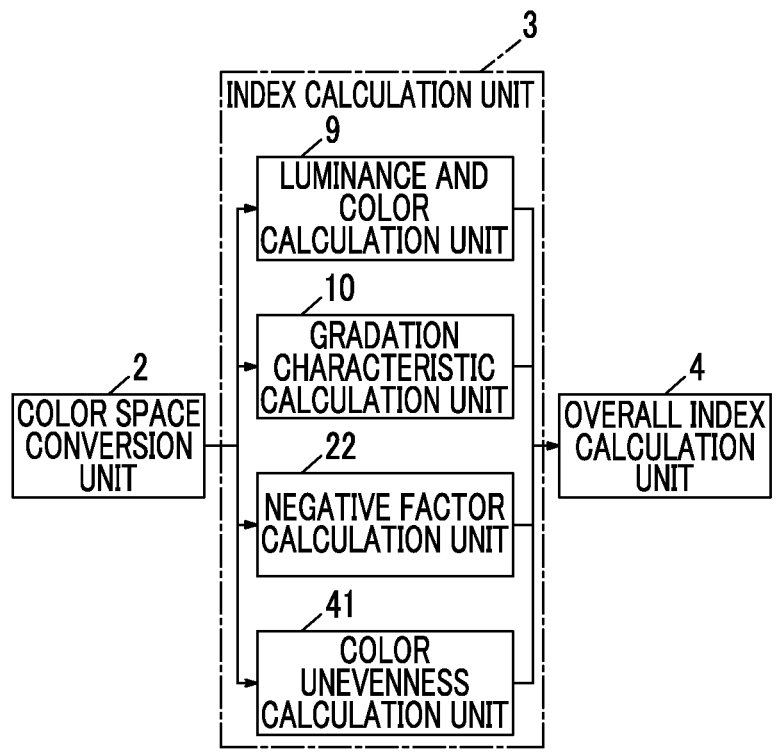
FIG. 16 is a block diagram illustrating a configuration of an index calculation unit of a transparency evaluation device according to Embodiment 4.

As illustrated in FIG. 16, in the transparency evaluation device according to Embodiment 3 illustrated in FIG. 10, a color unevenness calculation unit 41 is newly provided in the index calculation unit 3, and this color unevenness calculation unit 41 is connected to the color space conversion unit 2 and the overall index calculation unit 4, thereby forming the transparency evaluation device. That is, the index calculation unit 3 includes all of the luminance and color calculation unit, the gradation characteristic calculation unit, the negative factor calculation unit, and the color unevenness calculation unit shown in Embodiments 1 to 3.

Similarly, in the color unevenness calculation unit 41, an amount of generation of the color unevenness in the evaluation region R4 is calculated as a third skin evaluation index, and the third skin evaluation index is output to the overall index calculation unit 4.

In the overall index calculation unit 4, the value of the entire L* component and the value of the entire C* component in the evaluation region R1 are input from the luminance and color calculation unit 9, the smoothness of the change in the L* component in the evaluation region R2 is input from the gradation characteristic calculation unit 10, the number, the total area, and the area proportion of the negative factors are input from the negative factor calculation unit 22, and the total area and the area proportion of the color unevenness are input from the color unevenness calculation unit 41. The overall index calculation unit 4 combines the value of the entire L* component in the evaluation region R1, the value of the entire C* component in the evaluation region R1, the smoothness of the change in the L* component in the evaluation region R2, the number of the negative factors in the evaluation region R3, the total area of the negative factors in the evaluation region R3, the area proportion of the negative factors in the evaluation region R3, the total area of the color unevenness in the evaluation region R4, and the area rate of the color unevenness in the evaluation region R4, which have been input, with one another using a multiple regression equation or the like, thereby calculating the overall index for determining the evaluation for the transparency of the face F of the subject.

The transparency evaluation unit 5 evaluates the transparency of the face F of the subject based on the overall index calculated by the overall index calculation unit 4. A result of the evaluation is displayed on the display unit 6. Thus, it is possible to evaluate the transparency with high accuracy by evaluating the transparency based on a larger number of indices having different properties.

An example of an embodiment in which the transparency is actually evaluated using the transparency evaluation device according to Embodiment 4 described above is shown.

In this embodiment, the transparency is evaluated and sensory evaluation for transparency is performed on 8 subjects in their 40s using the transparency evaluation method of Embodiment 4. Here, in the transparency evaluation method of Embodiment 4, for each subject, the average value of the L* component in the evaluation region R1, the average value of the C* component in the evaluation region R1, the uniformity of the spacings of the plurality of contour lines partitioning the evaluation region R2, the total area of the freckles in the evaluation region R3, the total area of the pores in the evaluation region R3, and the total area of color unevenness in the evaluation region R4 are calculated and combined with one another to obtain an overall index for transparency.

Further, in a comparative example, the average value of the L* component in the evaluation region R1, the average value of the C* component in the evaluation region R1, the total area of the freckles in the evaluation region R3, the total area of the pores in the evaluation region R3, and the total area of the color unevenness in the evaluation region R4 are calculated for each subject and combined with one another to obtain an overall index for transparency. That is, for the overall index of Embodiment 4, an overall index is obtained using the indexes other than the uniformity of spacings of the plurality of contour lines partitioning the evaluation region R2.

Here, the multiple regression equation used when the overall index of Embodiment 4 is calculated was overall index=$188.9-536.0 \times L-17.3 \times C-19.6 \times F+64.3 \times P+186.5 \times I+62.0 \times K$. Further, the multiple regression equation used when the overall index of the comparative example is calculated was overall index=$189.7-532.1 \times L+72.0 \times C+185.4 \times F-109.7 \times P+99.6 \times I$. L indicates the average value of the L* component, C indicates the average value of the C* component, F indicates the total area of the freckles, P indicates the total area of the pores, I indicates the total area of color unevenness, and K indicates the uniformity of the contour line spacings.

Figure 17:
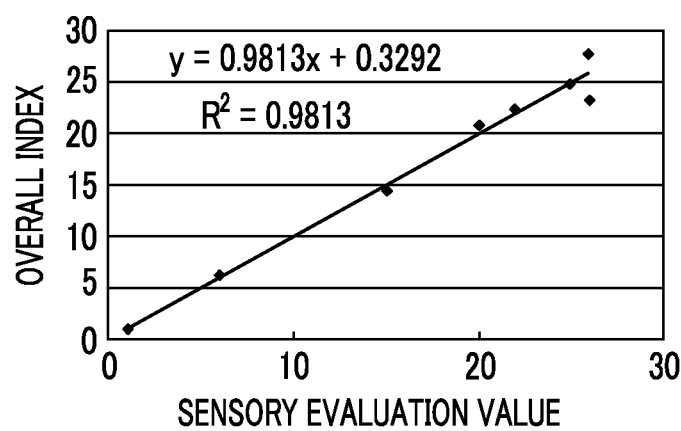
FIG. 17 is a diagram illustrating an obtained correlation between an overall index and a sensory evaluation value used in Embodiment 4.
Figure 18:
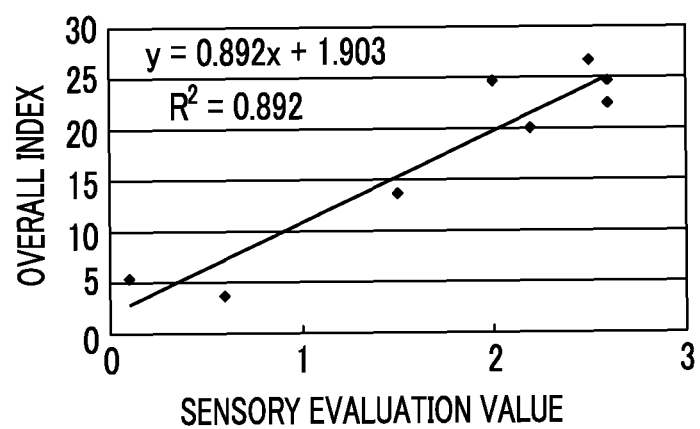
FIG. 18 is a diagram illustrating obtained correlation between an overall index and a sensory evaluation value used in a comparative example of Embodiment 4.

A graph obtained by plotting the overall index of Embodiment 4 with respect to the sensory evaluation value is illustrated in FIG. 17, and a graph obtained by plotting the overall index with respect to the sensory evaluation value in a comparative example is illustrated in FIG. 18. When the correlation between the overall index and the sensory evaluation value was obtained based on FIG. 17, the correlation coefficient $R^2$ was 0.98. Meanwhile, when the correlation between the overall index and the sensory evaluation value was obtained based on FIG. 18, the correlation coefficient $R^2$ was 0.89.

Thus, it can be seen that the overall index of Embodiment 4 has a sufficiently higher correlation with a sensory evaluation value than the overall index of the comparative example, and since the uniformity of spacings of the contour lines is added as an index for evaluating the transparency, it is possible to evaluate the transparency with high accuracy.

While the transparency has been evaluated for the face of the subject in Embodiments 1 to 4, it is possible to evaluate the transparency for the skin of a subject. For example, it is possible to evaluate the transparency for an arm or the like.

Further, the evaluation of the transparency of a bare skin as in Embodiments 1 to 4 may be executed by a transparency evaluation program recorded in a recording medium causing a computer including input means, a CPU, a memory, and the like to function. That is, by the transparency evaluation program recorded in the recording medium causing the computer to function, the image input unit acquires the captured image obtained by photographing the bare skin of the subject, and the CPU operates the preprocessing unit 1, the color space conversion unit 2, the index calculation unit 3, the overall index calculation unit 4, and the transparency evaluation unit 5 based on the acquired captured image to perform evaluation of the transparency for the bare skin of the subject.

Embodiment 5

While the transparency of the bare skin of the subject has been evaluated in Embodiments 1 to 4, the transparency of the face F (makeup skin) of a subject subjected to makeup can also be evaluated.

Figure 19:
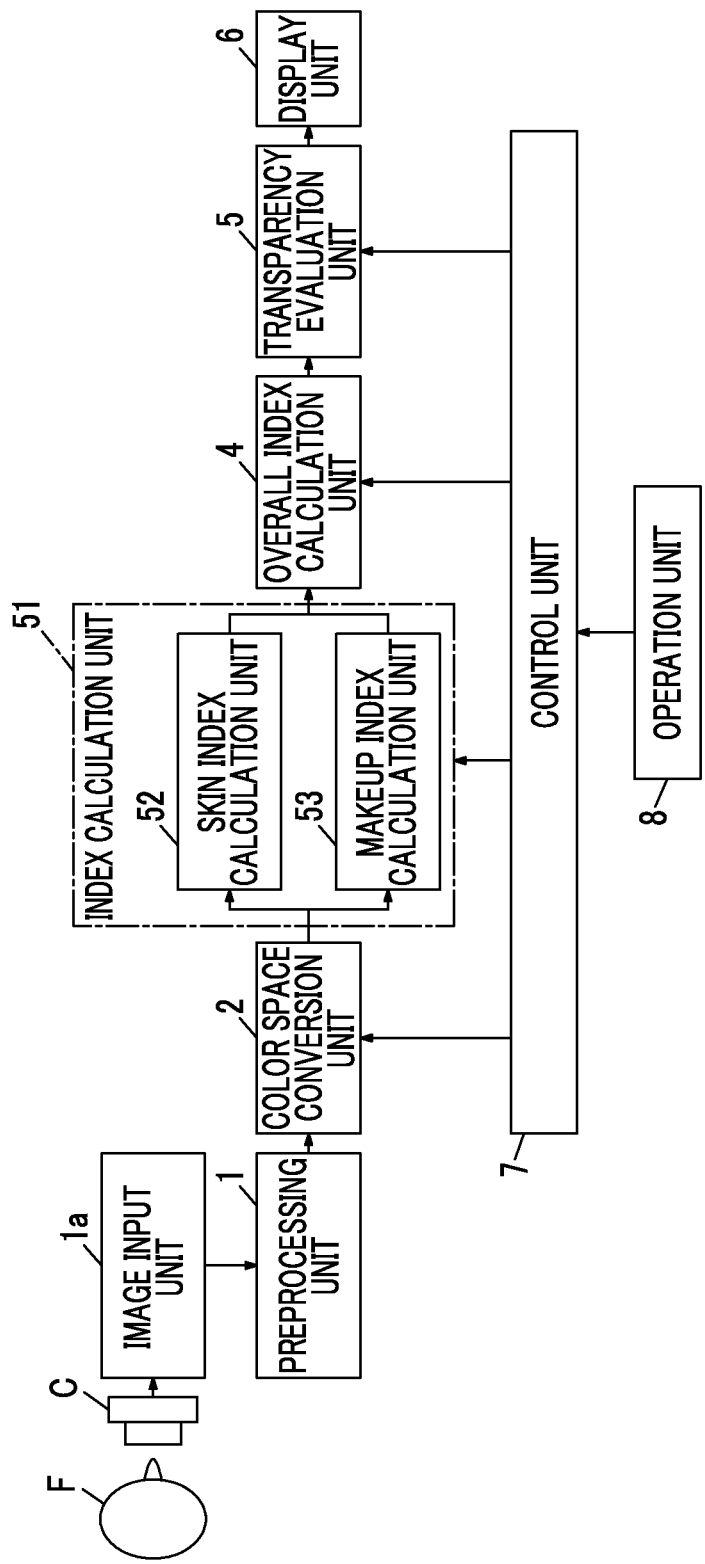
FIG. 19 is a block diagram illustrating a configuration of a transparency evaluation device according to Embodiment 5.

FIG. 19 illustrates a configuration of a transparency evaluation device according to Embodiment 5. This transparency evaluation device is obtained by arranging an index calculation unit 51 in place of the index calculation unit 3 in the transparency evaluation device of Embodiment 1 illustrated in FIG. 1. Specifically, the transparency evaluation device evaluates the transparency using a captured image obtained by photographing the face F of the subject subjected to makeup using a camera C, and includes an image input unit 1a connected to the camera C. A preprocessing unit 1, a color space conversion unit 2, an index calculation unit 51, an overall index calculation unit 4, a transparency evaluation unit 5, and a display unit 6 are sequentially connected to the image input unit 1a. Further, a control unit 7 is connected to the color space conversion unit 2, the index calculation unit 51, the overall index calculation unit 4, and the transparency evaluation unit 5, and an operation unit 8 is connected to the control unit 7.

The image input unit 1a receives the captured image from the camera C that has photographed the face F (madeup skin) of the subject subjected to makeup.

The preprocessing unit 1 performs preprocessing such as light amount correction and noise removal on the captured image input from the image input unit 1a.

The color space conversion unit 2 converts a color space of the captured image input from the preprocessing unit 1 to generate a color space-converted image.

The index calculation unit 51 includes a skin index calculation unit 52 and a makeup index calculation unit 53 connected to the color space conversion unit 2. The skin index calculation unit 52 and the makeup index calculation unit 53 receive the color space-converted image from the color space conversion unit 2, and calculate a skin evaluation index and a makeup evaluation index for evaluating the transparency of the madeup skin based on the color space-converted image, respectively.

Here, the skin evaluation index is an evaluation index common to the indexes of Embodiments 1 to 4 to evaluate the transparency of the bare skin, and is used to evaluate the transparency according to a perception when the madeup skin is viewed overall. On the other hand, the makeup evaluation index is an evaluation index specific to evaluation of the transparency of the madeup skin, and is a new index indicating a change in transparency due to the makeup. For example, an impasto impression of the makeup experienced when thick makeup is applied causes a decrease in transparency, and the makeup evaluation index can be determined based on the impasto impression.

The skin index calculation unit 52 and the makeup index calculation unit 53 output the calculated skin evaluation index and the calculated makeup evaluation index to the overall index calculation unit 4.

The overall index calculation unit 4 combines the skin evaluation index and the makeup evaluation index calculated by the skin index calculation unit 52 and the makeup index calculation unit 53 with each other to calculate the overall index for transparency.

The transparency evaluation unit 5 evaluates the transparency of the face F of the subject subjected to makeup based on the overall index calculated by the overall index calculation unit 4.

The display unit 6 includes, for example, a display device such as an LCD, and displays an evaluation result of the transparency evaluated by the transparency evaluation unit 5.

The operation unit 8 is used for the operator to perform an information input operation, and can be formed of a keyboard, a mouse, a trackball, a touch panel, or the like.

The control unit 7 performs control of each unit of the transparency evaluation device based on various instruction signals or the like input from the operation unit 8 by the operator.

Next, the skin index calculation unit 52 of the index calculation unit 51 will be described in detail.

Figure 20:
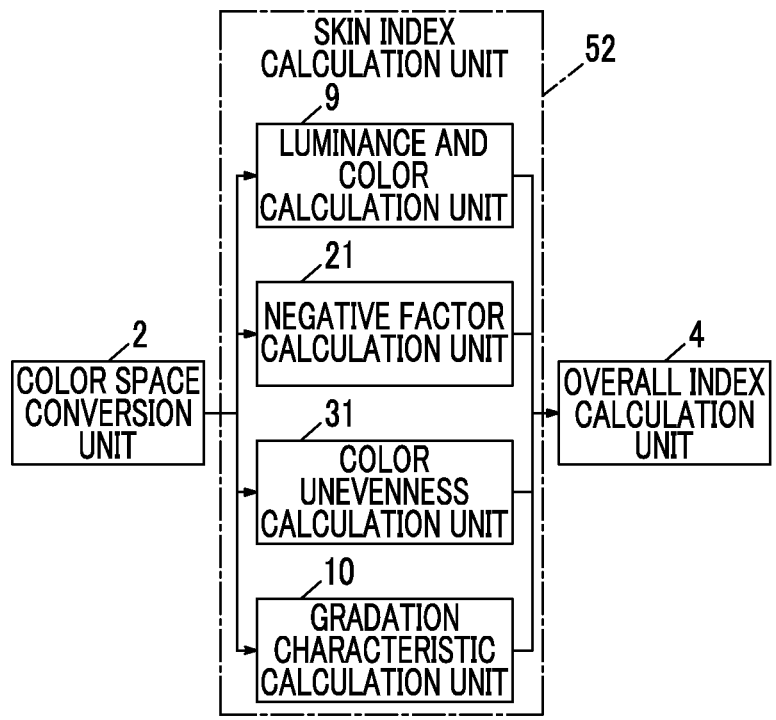
FIG. 20 is a block diagram illustrating a configuration of a skin index calculation unit of the transparency evaluation device according to Embodiment 5.

As illustrated in FIG. 20, the skin index calculation unit 52 includes a luminance and color calculation unit 9, a negative factor calculation unit 21, a color unevenness calculation unit 31, and a gradation characteristic calculation unit 10 connected to the color space conversion unit 2 and the overall index calculation unit 4.

The luminance and color calculation unit 9 sets the evaluation region R1 in the face of the subject subjected to makeup, and calculates a representative value of the luminance component or a representative value of the color component in the evaluation region R1, similar to the luminance and color calculation unit 9 of Embodiment 1. The evaluation region R1 may be set, for example, in the entire face F or the cheek portion. The representative value of the luminance component and the representative values of the color component can be calculated from, for example, the average value of the luminance component and the average value of the color component in the evaluation region R1, respectively.

The negative factor calculation unit 21 sets an evaluation region R3 in the face F of the subject subjected to makeup, detects negative factors such as freckles and pores in which a value of the luminance component or a value of the color component in the evaluation region R3 changes locally, and obtains an amount of generation of the negative factors, similar to the negative factor calculation unit 21 in Embodiment 2. The evaluation region R3 may be set in the entire face F or the cheek portion of the subject. Further, examples of the amount of generation of the negative factors may include the number, a total area, and an area proportion of negative factors.

The color unevenness calculation unit 31 sets an evaluation region R4 in the face F of the subject subjected to makeup, detects, as the color unevenness, a portion larger than the negative factors in the portion in which the value of the luminance component or the value of the color component in the evaluation region R4 changes locally, and obtains an amount of generation of the color unevenness, similar to the color unevenness calculation unit 31 of Embodiment 3. The evaluation region R4 may be set in, for example, the entire face F or the cheek portion of the subject. Further, examples of the amount of generation of the color unevenness may include a total area, an area proportion, and the number of instances of color unevenness.

The gradation characteristic calculation unit 10 sets an evaluation region R2 in the face F of the subject subjected to makeup, and calculates a gradation characteristic representing the smoothness of a change (gradation) in the luminance component in the evaluation region R2, similar to the gradation characteristic calculation unit 10 according to Embodiment 1. The evaluation region R2 may be set in, for example, a range from the cheek portion of the face F of the subject to an outline portion of the face F.

Next, the makeup index calculation unit 53 of the index calculation unit 51 will be described in detail.

Figure 21:
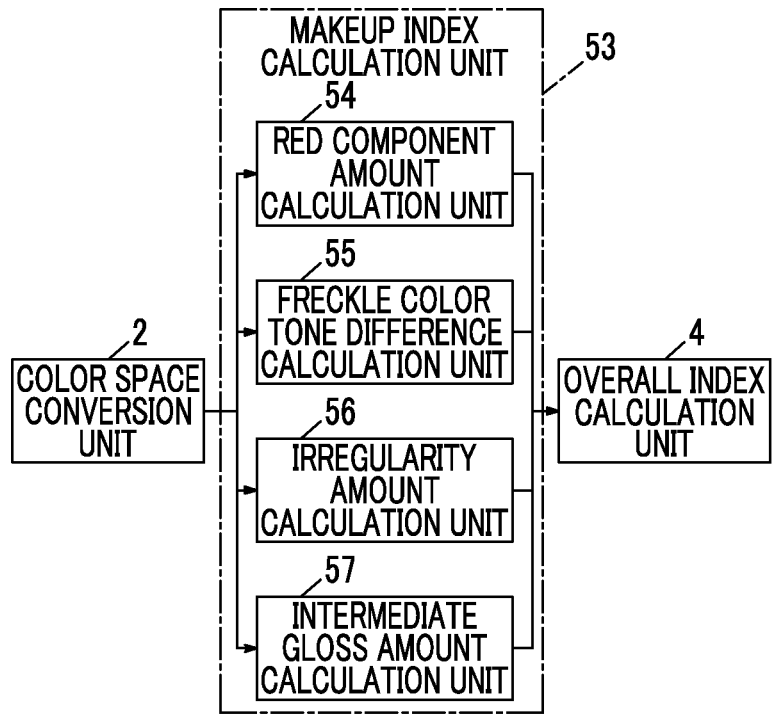
FIG. 21 is a block diagram illustrating a configuration of a makeup index calculation unit of the transparency evaluation device according to Embodiment 5.

As illustrated in FIG. 21, the makeup index calculation unit 53 includes a red component amount calculation unit 54, a freckle color tone difference calculation unit 55, an irregularity amount calculation unit 56, and an intermediate gloss amount calculation unit 57 connected to the color space conversion unit 2 and the overall index calculation unit 4.

The red component amount calculation unit 54 sets an evaluation region R5 in the face F of the subject subjected to makeup with respect to the color component image generated by the color space conversion unit 2. It is preferable for the evaluation region R5 to be set in at least one of a glabella portion, a cheek portion, and a jaw portion. The red component amount calculation unit 54 calculates an amount of the red component in the evaluation region R5 set in the color component image.

Here, the red component indicates redness due to complexion obviously appearing in a part of the face F of the subject, such as the glabella portion, the cheek portion, and the jaw portion, and may be obtained, for example, by extracting the a* component of the color component image. It is more preferable for the red component to be a component having a positive value among a* components of the color component image in order to reliably extract the redness due to complexion. Further, it is more preferable for the red component to be a component having a value equal to or greater than 13 and equal to or smaller than 30 among the a* components of the color component image in order to suppress erroneous detection of lips or the like having redness.

Further, the amount of red component may be calculated from an average value of the red component (for example, a* component) in the evaluation region R5, an area of a portion in which a value of the red component in the evaluation region R5 indicates a predetermined range (for example, a portion in which the value of the a* component is equal to or greater than 13 and equal to or smaller than 30), an area proportion of the portion in which the value of the red component in the evaluation region R5 indicates a predetermined range (for example, the portion in which the value of the a* component is equal to or greater than 13 and equal to or smaller than 30), or the like.

The red component amount calculation unit 54 outputs the amount of the red component in the evaluation region R5 as a makeup evaluation index to the overall index calculation unit 4.

The freckle color tone difference calculation unit 55 sets an evaluation region R6 in the face F of the subject subjected to makeup with respect to the luminance component image or the color component image generated by the color space conversion unit 2, and detects a freckle portion in which the value of the luminance component or the value of the color component changes locally in the set evaluation region R6. Here, it is preferable for the evaluation region R6 to be set in the entire face F or the cheek portion of the subject. Subsequently, the freckle color tone difference calculation unit 55 calculates a color tone difference between the freckle portion and surroundings thereof in the color component image.

The freckle color tone difference calculation unit 55 outputs the color tone difference between the freckle portion and surroundings thereof in the evaluation region R6 as a makeup evaluation index to the overall index calculation unit 4.

The irregularity amount calculation unit 56 sets an evaluation region R7 in the face F of the subject subjected to the makeup with respect to the luminance component image generated by the color space conversion unit 2, and detects a low luminance portion indicating a shadow generated in the face of the subject as an irregularity portion based on the value of the luminance component in the set evaluation region R7. For example, the irregularity amount calculation unit 56 may calculate a standard L* value in the face F of the subject, such as an average value of L* over the entire face F, subtract this average value of L* from the value of L* of the luminance component image generated by the color space conversion unit 2 for each pixel to generate a differential image and obtain ΔL*, and detect a low luminance portion in which ΔL*<3 in the differential image as an irregularity portion. When many noise components are included in the differential image, it is preferable to remove the noise components by performing an expansion process or the like on the image.

Further, it is preferable to detect the irregularity portion by further extracting a portion indicating wrinkles or pores based on a size or a shape in the detected low luminance portion. It is preferable for the evaluation region R7 to be set, for example, in at least one of an eye portion and a portion extending from a nose to a mouth. Subsequently, the irregularity amount calculation unit 56 calculates an amount of the detected irregularity portion in the evaluation region R7. Here, the amount of the irregularity portion can be calculated from an area (number of pixels) or an area proportion of the irregularity portion in the evaluation region R7.

The irregularity amount calculation unit 56 outputs the amount of the irregularity portion in the evaluation region R7 as a makeup evaluation index to the overall index calculation unit 4.

The intermediate gloss amount calculation unit 57 sets an evaluation region R8 in the face F of the subject subjected to makeup with respect to the luminance component image generated by the color space conversion unit 2, and detects an intermediate gloss portion having an approximately intermediate reflectance of light based on the intensity of the luminance component in the set evaluation region R8. Here, when a portion with high light reflectance in the madeup skin is a shiny portion and a portion with low light reflectance is a matte portion, the intermediate gloss portion indicates a gloss portion having a reflection of light between the shiny portion and the matte portion. It is preferable for the intermediate gloss portion to be a portion in which the intensity of the luminance component exhibits a value equal to or greater 60 and equal to or smaller than 70. Further, it is preferable for the evaluation region R8 to be set, for example, in at least one of a cheekbone portion and a nose ridge portion.

Subsequently, the intermediate gloss amount calculation unit 57 calculates an amount of the intermediate gloss portion detected in the evaluation region R8. Here, the amount of the intermediate gloss portion can be calculated from an area (number of pixels) or an area proportion of the intermediate gloss portion in the evaluation region R8.

The intermediate gloss amount calculation unit 57 outputs the amount of the intermediate gloss portion in the evaluation region R8 as a makeup evaluation index to the overall index calculation unit 4.

Next, an operation of Embodiment 5 will be described.

First, a captured image obtained by photographing the face F of the subject subjected to makeup using the camera C is input from the camera C to the preprocessing unit 1 via the image input unit 1a of the transparency evaluation device, as illustrated in FIG. 19, similar to Embodiments 1 to 4. The captured image is subjected to preprocessing in the preprocessing unit 1, and then, the color space-converted image is generated by the color space conversion unit 2. The color space conversion unit 2 extracts the luminance component and the color component from the color space-converted image, and generates the luminance component image and the color component image. For example, the color space conversion unit 2 may generate the L* component image as the luminance component image and generate the C* component image, the a* component image, and a Hue component image as the color component image.

The color space conversion unit 2 outputs the generated L* component image and the generated C* component image to the luminance and color calculation unit 9, the negative factor calculation unit 21, the color unevenness calculation unit 31, and the gradation characteristic calculation unit 10 of the skin index calculation unit 52.

The luminance and color calculation unit 9 sets the evaluation region R1 in the cheek portion of the face F of the subject subjected to makeup with respect to the L* component image and the C* component image, similar to, for example, the setting of the evaluation region R1 illustrated in FIG. 2. Subsequently, the luminance and color calculation unit 9 obtains an average value of the intensity of the L* component with respect to the evaluation region R1 set in the L* component image, and obtains an average value of the intensity of the C* component with respect to the evaluation region R1 set in the C* component image. Accordingly, with respect to the evaluation region R1 set in the face F of the subject, the value of the entire L* component and the value of the entire C* component can be obtained.

As described above, it is known that a skin of a person is white and has a bright color and a low chroma when the person is young, but becomes an overall yellowish and dark skin with overall low transparency due to aging. This change in luminance and chroma provides the same impression in the madeup skin. Therefore, the value of the entire L* component and the value of the entire C* component of the evaluation region R1 obtained by the luminance and color calculation unit 9 are considered as indexes indicating a change in transparency of the madeup skin. Specifically, when the value of the entire L* component is large (bright), the transparency of the face F of the subject subjected to makeup is experienced as being high, and when the value of the entire C* component is small, the transparency of the face F of the subject subjected to makeup is experienced as being high. Therefore, the average value of the L* component and the average value of the C* component in the evaluation region R1 are output as skin evaluation indexes for evaluating the transparency of each madeup skin from the luminance and color calculation unit 9 to the overall index calculation unit 4.

The average value of the L* component and the average value of the C* component in the evaluation region R1 used as the skin evaluation index are physical amounts close to the perception when the entire face F of the subject is viewed, and provide an objective index close to sensory evaluation for evaluation of the transparency.

The negative factor calculation unit 21 sets the evaluation region R3 in the cheek portion of the face F of the subject subjected to makeup with respect to the L* component image, and detects negative factors such as freckles and pores in which the value of the L* component changes locally in the set evaluation region R3. Here, the negative factors may be specified by generating a Dog image and extracting the freckles and pores, similar to the negative factor calculation unit 21 of Embodiment 2.

Subsequently, the negative factor calculation unit 21 calculates an amount of generation of negative factors such as the number, the total area, and the area proportion of the negative factors based on a result of detecting the negative factors in the evaluation region R3. Negative factors are generated with aging, and when the amount of generation thereof is small, the transparency of the face F of the subject subjected to makeup is experienced as being high. For freckles among the negative factors, a concentration of the color greatly affects the transparency, and accordingly, a concentration of the freckles with respect to the surrounding madeup skin can be calculated as an amount of generation of negative factors. The concentration of the freckles can be obtained, for example, by obtaining an average value of the color component of the entire evaluation region R3, obtaining an average value of the color component of the freckle portion detected in the evaluation region R3, and calculating a difference (color difference) between the average value of the color component of the entire evaluation region R3 and the average value of the color component of the freckle portion.

Thus, the calculated amount of generation of the negative factors in the evaluation region R3 is output as the skin evaluation index from the negative factor calculation unit 21 to the overall index calculation unit 4.

The amount of generation of the negative factors in the evaluation region R3 used as the skin evaluation index is a physical amount close to the perception when the entire face F of the subject is viewed, and the skin evaluation index provides an objective index close to the sensory evaluation for evaluation of transparency.

The color unevenness calculation unit 31 sets the evaluation region R4 in the face F of the subject subjected to makeup with respect to the L* component image, and detects a part in which the value of the L* component changes locally in the set evaluation region R4 and that is larger than the negative factor, as color unevenness. Here, the color unevenness can be extracted by generating a Dog image, as in the color unevenness calculation unit 31 of Embodiment 3. Further, the evaluation region R4 can be set in the entire face F or in the cheek portion of the subject.

Subsequently, the color unevenness calculation unit 31 calculates an amount of generation of the color unevenness such as a total area and an area proportion of the color unevenness, based on a result of detecting the color unevenness in the evaluation region R4. This color unevenness is generated with aging, and when the amount of generation thereof is small, transparency of the face F of the subject subjected to makeup is experienced as being high. Therefore, the color unevenness calculation unit 31 outputs the amount of generation of the color unevenness in the evaluation region R4 as a skin evaluation index to the overall index calculation unit 4.

The amount of generation of the color unevenness in the evaluation region R4 used as this skin evaluation index is a physical amount close to the perception when the entire face F of the subject is viewed, and the skin evaluation index provides an objective index close to the sensory evaluation for evaluation of transparency.

The gradation characteristic calculation unit 10 obtains an intensity distribution of the luminance component with respect to a predetermined evaluation region R2 of the L* component image, and calculates the gradation characteristic representing the smoothness of the change in the luminance component over the evaluation region R2 based on the obtained intensity distribution, similar to the gradation characteristic calculation unit 10 according to Embodiment 1.

Figure 22A:
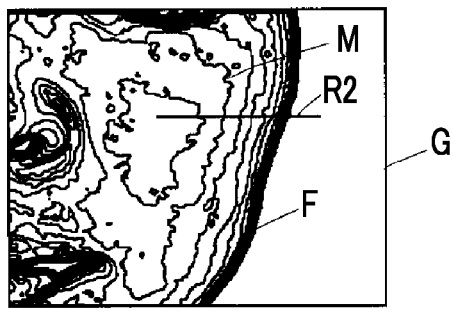
FIG. 22A is a diagram illustrating an L* component contour line distribution image in Embodiment 5 of a subject with high transparency.
Figure 22B:
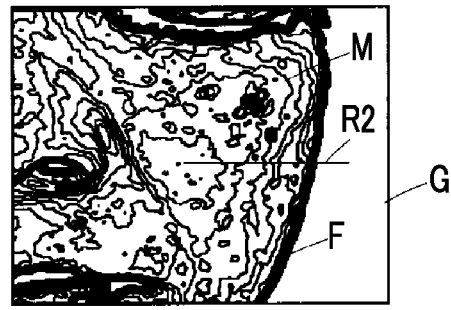
FIG. 22B is a diagram illustrating an L* component contour line distribution image of a subject with low transparency.

Specifically, the gradation characteristic calculation unit 10 sets a plurality of stepwise contour lines M with uniform intensity spacings in the face F of the subject of the L* component image, and generates an L* component contour line distribution image G obtained by partitioning the face F of the subject according to the value of the L* component using the plurality of contour lines M, as illustrated in FIGS. 22A and 22B. Here, FIG. 22A illustrates the L* component contour line distribution image G of a subject with high transparency of the madeup skin, and FIG. 22B illustrates the L* component contour line distribution image G of a subject with low transparency of the madeup skin. Thus, by partitioning the face F of the subject subjected to makeup using the plurality of contour lines, the distribution of the L* component in the face F of the subject subjected to makeup can be represented using the positions of the plurality of contour lines.

It is preferable for the plurality of contour lines M partitioning the face F of the subject to be set with an intensity spacing of about 1/10 with respect to an intensity range of the L* component image, or with an increment of 3 to 5 digits.

Subsequently, the gradation characteristic calculation unit 10 sets the evaluation region R2 so that a linear connection from the cheek portion of the face F of the subject to an outline portion of the face F is made with respect to the L* component contour line distribution image G. In this case, it is preferable for the evaluation region R2 to be set to pass through a portion in which the value of the L* component is largest in the cheek portion of the face F of the subject. For example, the evaluation region R2 may be set in a region linearly connecting a position at which the value of the L* component is largest in the cheek portion to the outline portion of the face F in a horizontal direction. Further, the evaluation region R2 may be set in a region linearly connecting the position at which the value of the L* component is largest in the cheek portion to the outline portion of the face F to be substantially perpendicular to and intersect the plurality of contour lines.

Figure 23A:
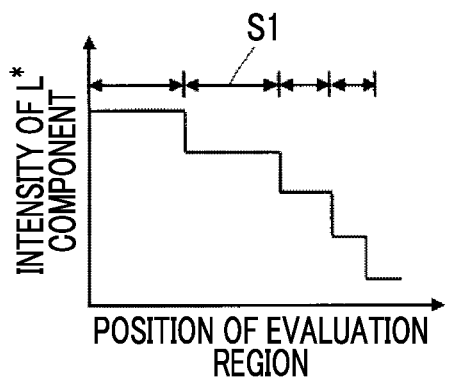
FIG. 23A is a diagram illustrating a change in the L* component in an evaluation region set in the L* component contour line distribution image in Embodiment 5 of a subject with high transparency.
Figure 23B:
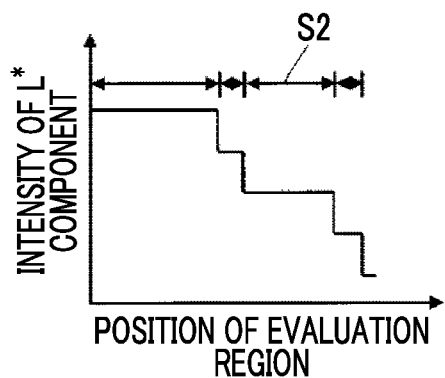
FIG. 23B is a diagram illustrating a change in the L* component in an evaluation region set in the L* component contour line distribution image of a subject with low transparency.

Thus, the change in the L* component in the evaluation region R2 set in the L* component contour line distribution image G (FIG. 22A) of the subject with high transparency of the madeup skin is illustrated in FIG. 23A, and the change in the L* component in the evaluation region R2 set in the L* component contour line distribution image G (FIG. 22B) of the subject with low transparency of the madeup skin is illustrated in FIG. 23B. As illustrated in FIGS. 23A and 23B, it can be seen that the change in the L* component in the evaluation region R2 of the subject with high transparency of the madeup skin is a smooth decrease while drawing a certain curve along a curvature of the face F with respect to the change in the L* component of the subject with low transparency of the madeup skin. Accordingly, the gradation characteristic representing the smoothness of the change in the L* component may be a skin evaluation index for evaluating the transparency.

Spacings of a plurality of contour lines M adjacent to each other in the evaluation region R2 are obtained, and the gradation characteristic of the L* component may be calculated based on the uniformity of the obtained spacings of the plurality of contour lines M, as in the gradation characteristic calculation unit 10 according to Embodiment 1.

Further, the gradation characteristic of the L* component may also be calculated based on the number of the plurality of contour lines M partitioning the evaluation region R2.

The gradation characteristic of the L* component obtained in this manner is output as a skin evaluation index from the gradation characteristic calculation unit 10 to the overall index calculation unit 4.

This skin evaluation index is intended to evaluate the transparency based on a change in the luminance of the face F of the subject subjected to makeup, unlike the evaluation index for evaluating the transparency based on, for example, the luminance of the face F of the subject subjected to makeup, and can be used to evaluate the transparency from a different viewpoint from the above-described skin evaluation index. Further, the gradation characteristic of the L* component used in the skin evaluation index is a physical amount close to the perception when the entire face F of the subject is viewed, similar to the skin evaluation index described above, and the skin evaluation index provides an objective index close to sensory evaluation for evaluation of the transparency.

Meanwhile, the color space conversion unit 2 outputs the L* component image, the C* component image, the a* component image, and the Hue component image to the red component amount calculation unit 54, the freckle color tone difference calculation unit 55, the irregularity amount calculation unit 56, and the intermediate gloss amount calculation unit 57 of the makeup index calculation unit 53.

Figure 24:
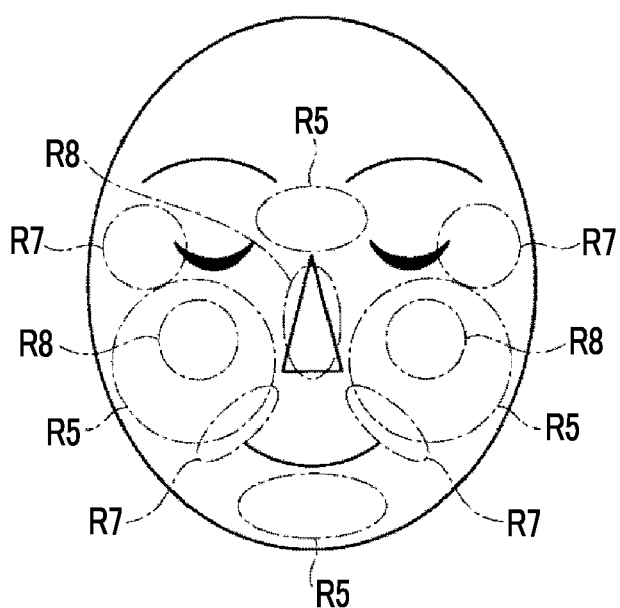
FIG. 24 is a diagram illustrating an evaluation region set in a face of the subject in Embodiment 5.

The red component amount calculation unit 54 sets the evaluation region R5 in the glabella portion, the cheek portion, and the jaw portion of the face F of the subject subjected to makeup, as illustrated in, for example, FIG. 24, with respect to the a* component image input from the color space conversion unit 2.

Figure 25A:
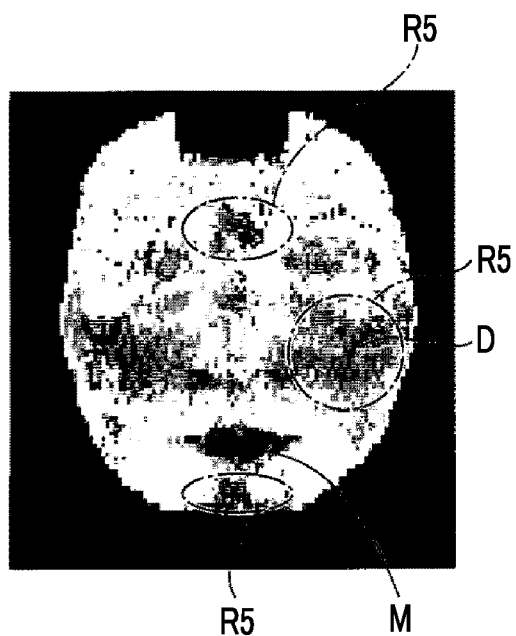
FIG. 25A is a diagram illustrating an a* component image of the madeup skin in Embodiment 5 with high transparency.
Figure 25B:
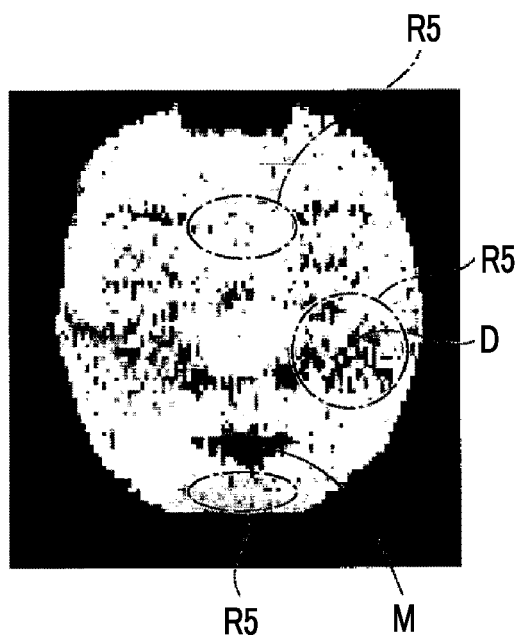
FIG. 25B is a diagram illustrating an a* component image of the madeup skin of a subject with low transparency.

Here, the a* component image of the madeup skin in which it is evaluated through the sensory evaluation that the transparency is high with respect to the madeup skin when a foundation is applied to the face F of the subject is illustrated in FIG. 25A, and the a* component image of the madeup skin in which it is evaluated through the sensory evaluation that the transparency is low is illustrated in FIG. 25B. It can be seen that in FIG. 25A, a large number of red components D (black portions) are distributed in the glabella portion, the cheek portion, and the jaw portion in which the evaluation region R5 is set, whereas in FIG. 25B, the red components D are hardly distributed in the glabella portion, the cheek portion, and the jaw portion in which the evaluation region R5 is set.

In general, in a state of a bare skin, redness (red component) due to complexion is known to be generated obviously in the glabella portion, the cheek portion, and the jaw portion. As illustrated FIG. 25A, when the redness caused by the complexion is observed even after a foundation is applied, it is considered that it is difficult for an unnatural change due to makeup to be experienced, and high transparency is obtained due to an effect of adjustment of a skin color due to the foundation. On the other hand, as illustrated FIG. 25B, when the redness caused by the complexion is not observed even after the foundation is applied, the unnatural change due to makeup increases. This unnatural change causes, for example, an impasto impression of impasto of the foundation, and the transparency is experienced as being low.

Therefore, the red component amount calculation unit 54 calculates an amount of a red component in the evaluation region R5 set in the a component image. This amount of the red component is an index indicating a decrease in the transparency due to the makeup, and when a value thereof is low, the transparency of the madeup skin is experienced as being low. The amount of the red component may be calculated from an average value of values of the a* component, an area of a portion in which the value of the a* component is equal to or greater than 13 and equal to or smaller than 30, an area proportion of the portion in which the value of the a* component is equal to or greater than 13 and equal to or smaller than 30, or the like. Here, in FIGS. 25A and 25B, a lip portion M exhibits the red component, but since the value of the a* component is equal to or greater than 13 and equal to or smaller than 30, the red component other than the lip portion M can be extracted.

Subsequently, the red component amount calculation unit 54 outputs the amount of the red component in the evaluation region R5 as a makeup evaluation index for evaluating the transparency of the madeup skin to the overall index calculation unit 4.

The amount of the red component used in the makeup evaluation index is not commonly used when the transparency of the bare skin is evaluated, like the skin evaluation index described above, is an evaluation index specific to the madeup skin exhibiting a decrease in the transparency due to the makeup, and can be used to evaluate the transparency from a different viewpoint from the skin evaluation index.

The freckle color tone difference calculation unit 55 sets the evaluation region R6 in the cheek portion of the face F of the subject subjected to makeup with respect to the L* component image input from the color space conversion unit 2, and detects the freckle portion in which the value of the L* component in the set evaluation region R6 changes locally. The freckle portion may be detected from a Dog image or the like, as in the negative factor calculation unit 21.

Here, the color tone difference between the freckle portion and the surroundings thereof may increase due to makeup of the face F of the subject. For example, when a foundation is applied to the face F of the subject, the color of the skin is uniformly adjusted as a whole due to the foundation, whereas the color of the foundation overlaps the color of the freckle portion, and unnatural color such as gray may be partially generated. A difference between the unnatural color of this freckle portion and a color of the surroundings uniformly adjusted by the foundation is large, and this color tone difference causes an impasto impression of makeup impasto or the like, and the transparency is experienced as being low.

Accordingly, the freckle color tone difference calculation unit 55 calculates a color tone difference between the detected freckle portion and the surroundings thereof using, for example, the Hue component image. This color tone difference is an index indicating a decrease in the transparency due to makeup, and when the difference is high, the transparency of the madeup skin is experienced as being low. The freckle color tone difference calculation unit 55 outputs the color tone difference between the freckle portion and the surrounding thereof in the evaluation region R6 as a makeup evaluation index for evaluating the transparency of the madeup skin to the overall index calculation unit 4.

The color tone difference between the freckle portion and surroundings thereof used as the makeup evaluation index is not commonly used when the transparency of the bare skin is evaluated like the skin evaluation index described above, is an evaluation index specific to the madeup skin exhibiting a decrease in the transparency due to makeup, and can be used to evaluate the transparency from a different viewpoint from the skin evaluation index.

The irregularity amount calculation unit 56 sets the evaluation region R7 in an eye portion and a portion extending from a nose to a mouth of the face F of the subject subjected to makeup with respect to the L* component image input from the color space conversion unit 2, for example, as illustrated in FIG. 24. The irregularity amount calculation unit 56 detects an irregularity portion in which a value of the L* component in the set evaluation region R7 is equal to or smaller than a predetermined threshold value.

Figure 26A:
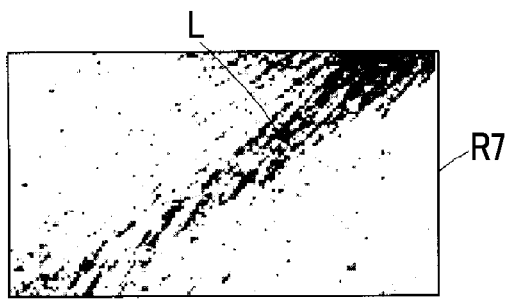
FIG. 26A is a diagram illustrating an image obtained by extracting low luminance portions from an L* component image in Embodiment 5 with high transparency.
Figure 26B:
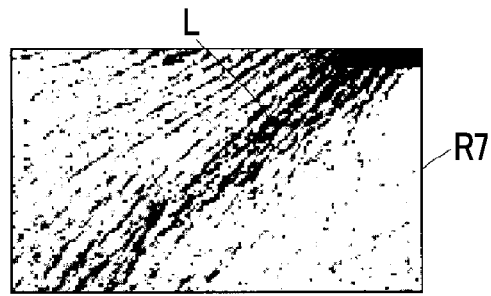
FIG. 26B is a diagram illustrating an image obtained by extracting low luminance portions from an L* component image of a subject with low transparency.

Here, FIGS. 26A and 26B illustrate results of extracting a low luminance portion L in which the value of the L* component is equal to or smaller than a predetermined threshold value in the eye portion of the madeup skin in which the face F of the subject is coated with foundation. FIG. 26A is a madeup skin in which the transparency is evaluated to be high in the sensory evaluation, and FIG. 26B is a madeup skin in which the transparency is evaluated to be low in the sensory evaluation. As a result, it can be seen that in FIG. 26A, there are a small number of low luminance portions L in the eye portion in which the evaluation region R7 is set, whereas in FIG. 26B, there are a large number of low luminance portions L in the eye portion in which the evaluation region R7 is set.

In general, it is known that, for example, when an amount of application of foundation is large, the foundation is deposited in an irregularity portion such as a wrinkle portion, and a shadow or the like is generated. Accordingly, the low luminance portion L is reduced and the irregularity portion is noticeable. As illustrated in FIG. 26A, when there are a small number of low luminance portions L in the madeup skin and the irregularity portion is not noticeable, it is considered that it is difficult for an unnatural change due to makeup to be experienced, and high transparency is obtained due to an effect of adjustment of a skin color due to the foundation. On the other hand, as illustrated in FIG. 26B, when there are a large number of low luminance portions L in the madeup skin and the irregularity portion is noticeable, the unnatural change due to makeup increases. This unnatural change causes, for example, an impasto impression of impasto of the foundation, and accordingly, the transparency is experienced as being low.

Therefore, the irregularity amount calculation unit 56 calculates the amount of the irregularity portion detected in the evaluation region R7. The amount of the irregularity portion is a new evaluation index indicating a decrease in the transparency due to makeup, and when a value thereof is high, the transparency of the madeup skin is experienced as being, low. The amount of the irregularity portion may be calculated from an area, an area proportion, or the like of the irregularity portion in the evaluation region R7.

Subsequently, the irregularity amount calculation unit 56 outputs the amount of irregularity portion in the evaluation region R7 as a makeup evaluation index for evaluating the transparency of the madeup skin to the overall index calculation unit 4.

A phenomenon in which the irregularity portion is noticeable after the makeup is applied obviously appears when using a powder cosmetic, and it is preferable that the makeup evaluation index calculated by the irregularity amount calculation unit 56 is used when a powder cosmetic is used.

The amount of the irregularity portion used as the makeup evaluation index is not commonly used when the transparency of the hare skin is evaluated unlike the skin evaluation index described above, is an evaluation index specific to the madeup skin exhibiting a decrease in the transparency due to makeup, and can be used to evaluate the transparency from a different viewpoint from the skin evaluation index.

The intermediate gloss amount calculation unit 57 sets an evaluation region R8 in a cheekbone portion and a nose ridge portion of the face F of the subject subjected to makeup, and detects the intermediate gloss portion having an approximately intermediate reflectance of light in the set evaluation region R8 based on the intensity of the L* component with respect to the L* component image input from the color space conversion unit 2, as illustrated in, for example, FIG. 24. The intermediate gloss portion may be obtained, for example, by detecting a portion in which the intensity of the L* component exhibits a value equal to or greater than 60 and equal to or smaller than 70.

In general, an intermediate gloss portion, that is, a so-called gloss is known to be generated in cheekbone and nose ridge portions in a state of a bare skin, but the intermediate gloss portion may be reduced due to makeup of the face F of the subject. For example, when a foundation is applied to the face F of the subject, the color of the skin is uniformly adjusted as a whole due to the foundation, whereas the gloss is decreased or increased. Specifically, when a foundation with low gloss is applied, the gloss is decreased, and when liquid foundation is applied, the gloss is increased. With the decrease or increase in gloss, the intermediate gloss portion is unnaturally reduced, an impasto impression of the makeup or the like is caused, and the transparency is experienced as being low.

Thus, the intermediate gloss amount calculation unit 57 calculates an amount of the intermediate gloss portion detected in the evaluation region R8. The amount of the intermediate gloss portion is an index indicating a decrease in the transparency due to the makeup, and when a value thereof is low, the transparency of the madeup skin is experienced as being low. The amount of the intermediate gloss portion can be calculated from an area, an area proportion, or the like of the intermediate gloss portion in the evaluation region R8.

Subsequently, the intermediate gloss amount calculation unit 57 outputs the amount of the intermediate gloss portion in the evaluation region R8 as a makeup evaluation index for evaluating the transparency of the madeup skin to the overall index calculation unit 4.

A phenomenon in which the intermediate gloss portion is decreased after the makeup is applied obviously appears by using a liquid cosmetic, and it is preferable that the makeup evaluation index calculated by the intermediate gloss amount calculation unit 57 is used when the liquid cosmetic is used.

The amount of the intermediate gloss portion used as the makeup evaluation index is not commonly used when the transparency of the bare skin is evaluated unlike the skin evaluation index described above, is an evaluation index specific to the madeup skin exhibiting a decrease in the transparency due to makeup, and can be used to evaluate the transparency from a different viewpoint from the skin evaluation index.

Thus, the five skin evaluation indexes calculated by the luminance and color calculation unit 9, the negative factor calculation unit 21, the color unevenness calculation unit 31, and the gradation characteristic calculation unit 10 are input to the overall index calculation unit 4, and the four makeup evaluation indexes calculated by the red component amount calculation unit 54, the freckle color tone difference calculation unit 55, the irregularity amount calculation unit 56, and the intermediate gloss amount calculation unit 57 are input to the overall index calculation unit 4.

The overall index calculation unit 4 performs linear summation on the five skin evaluation indexes and the four makeup evaluation indexes that have been input, that is, the five skin evaluation indexes including the value of the entire L* component of the evaluation region R1, the value of the entire C* component of the evaluation region R1, the amount of generation of the negative factors in the evaluation region R3, the amount of generation of the color unevenness in the evaluation region R4, and the gradation characteristic of the L* component of the evaluation region R2, and the four makeup evaluation indexes including the amount of the red component of the evaluation region R5, the color tone difference between the freckle portion in the evaluation region R6 and surroundings thereof, the amount of the irregularity portion of the evaluation region R7, and the amount of the intermediate gloss portion in the evaluation region R8, for example, using a multiple regression equation obtained by performing sensory evaluation in advance to combine the indexes with one another, and to calculate an overall index for overall evaluation of the transparency of the face F of the subject subjected to makeup. Here, the skin evaluation index represents the transparency when the face F of the subject subjected to makeup is viewed as a whole, whereas the makeup evaluation index represents a decrease in the transparency due to makeup. The overall index may be expressed by subtracting the four makeup evaluation indexes from the five skin evaluation indexes. The value of the calculated overall index is output from the overall index calculation unit 4 to the transparency evaluation unit 5.

The transparency evaluation unit 5 evaluates the transparency of the face F of the subject subjected to makeup based on the overall index calculated by the overall index calculation unit 4, and a result of evaluation is displayed on the display unit 6.

According to this embodiment, since the transparency is objectively evaluated according to a perception when the face F of the subject subjected to makeup is viewed as a whole based on the overall index in which the skin evaluation index and the makeup evaluation index are combined with each other, it is possible to obtain an evaluation result sufficiently coincident with the evaluation of the transparency through the sensory evaluation. Further, the skin evaluation index calculated based on the change in the luminance component in the gradation characteristic calculation unit 10 is a new index that is not in the related art. It is possible to achieve evaluation closer to the evaluation of the transparency through sensory evaluation by evaluating the transparency of the madeup skin based on the overall index in which this skin evaluation index is added.

Further, the makeup evaluation index calculated by the makeup index calculation unit 53 is an evaluation index specific to the madeup skin showing a change in transparency due to the makeup. It is possible to accurately evaluate the transparency of the madeup skin in combination with the skin evaluation index.

Embodiment 6

Figure 27:
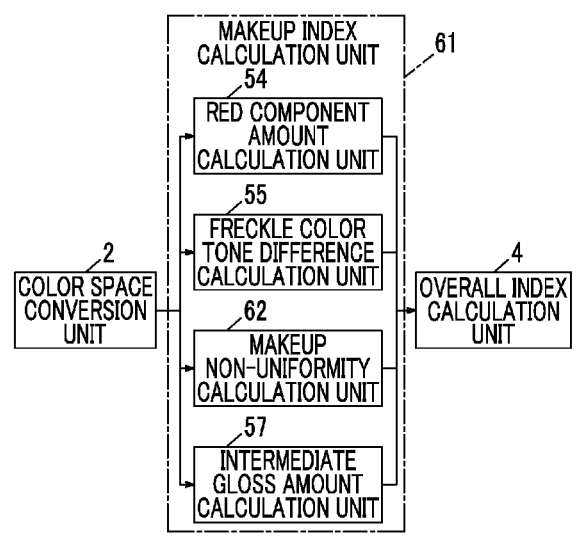
FIG. 27 is a block diagram illustrating a configuration of a makeup index calculation unit of a transparency evaluation device according to Embodiment 6.

FIG. 27 illustrates a configuration of the makeup index calculation unit 61 of the transparency evaluation device according to Embodiment 6. In this makeup index calculation unit 61, a makeup non-uniformity calculation unit 62 is connected to the color space conversion unit 2 and the overall index calculation unit 4 in place of the irregularity amount calculation unit 56 in the makeup index calculation unit 53 of the transparency evaluation device according to Embodiment 5.

Figure 28:
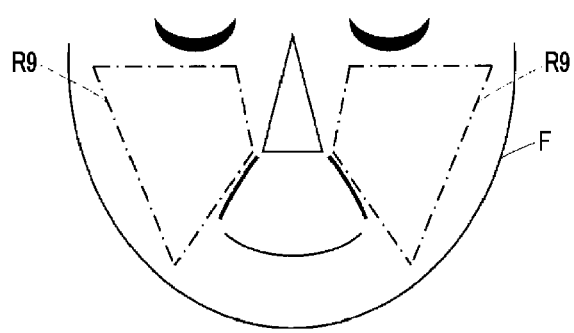
FIG. 28 is a diagram illustrating an evaluation region set in a face of a subject in a makeup non-uniformity calculation unit of Embodiment 6.

The makeup non-uniformity calculation unit 62 sets an evaluation region R9 in the face F of the subject subjected to makeup with respect to the captured image. It is preferable for the evaluation region R9 to be set in the cheek portion from lower sides of the eyes to upper sides of smile lines (wrinkles extending from a nostril to corners of the mouth), as illustrated in FIG. 28.

Subsequently, the makeup non-uniformity calculation unit 62 extracts a luminance component derived from the makeup or a color component derived from the makeup from the evaluation region R9 of the captured image based on the value of the luminance component derived from the skin and the value of the luminance component derived from the makeup that are different from each other, or the value of the color component derived from the skin and the value of the color component derived from the makeup that are different from each other.

Here, as the captured image, the luminance component or the color component derived from the makeup may be extracted. For example, the captured image input from the camera C, the L* component image generated by the color space conversion unit 2, or the like may be used. In particular, it is preferable to extract the color component derived from the makeup using a G channel among RGB channels of the captured image input from the camera C. In a wavelength region of the G channel, such as a wavelength region from 480 n to 600 nm, a difference between an intensity of the color component derived from the skin and an intensity of the color component derived from the makeup appears to be great, and accordingly, it is possible to easily extract the color component derived from the makeup using this G channel image. It is preferable for the wavelength region of the G channel to be set to approximately 550 nm, and accordingly, the difference between the intensity of the color component derived from the skin and the intensity of the color component derived from the makeup increases, such that the color component derived from the makeup can be extracted with high accuracy.

Subsequently, the makeup non-uniformity calculation unit 62 extracts a non-uniform portion in which the value of the luminance component derived from the makeup or the value of the color component derived from the makeup changes non-uniformly in the luminance component derived from the makeup or the color component derived from the makeup, which have been extracted from the captured image, and calculates a degree of non-uniformity of the makeup in the evaluation region R9.

Here, the non-uniform portion of the makeup is generated due to a small mass generated by applying a foundation to the face F of the subject. Specifically, a mass generated by the foundation being compacted in a particle shape on a surface of the skin when the foundation is applied, a mass of the foundation entering pores, a mass of the foundation attached to an edge of a skin groove, and the like give a white stand-out impression relative to the color of surroundings adjusted by the foundation. This non-uniform portion of the makeup causes unnatural powder impression, an impasto impression, and the like due to the makeup, and the transparency is experienced as being low.

Therefore, the makeup non-uniformity calculation unit 62 may generate a smoothed image in which a non-uniform portion of the makeup has been removed by performing a smoothing process on the G channel image, and generate a differential image by performing subtraction on the G channel image and the smoothed image for each pixel, to thereby easily extract the non-uniform portion of the makeup. It is preferable for the smoothing process to be performed so that a portion having a spatial frequency equal to or lower than 0.1 cycle/mm is removed and more non-uniform portions of the makeup are removed. For example, the smoothing process can be performed using a Gaussian filter. Further, it is preferable that in the differential image, the non-uniform portion of the makeup is clarified by generating the binarized image through a binarization process. In the binarization process, for example, a threshold value may be −30 for intensity of the differential image.

Figure 29A:
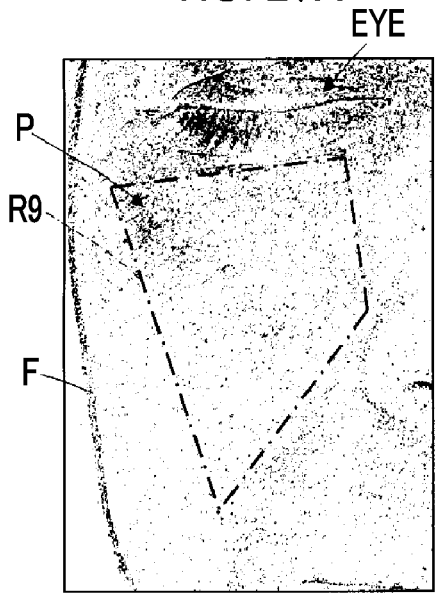
FIG. 29A is a diagram illustrating a binarized image in which non-uniform portions of makeup are detected in Embodiment 6 in which there are a small number of non-uniform portions of makeup.
Figure 29B:
FIG. 29B is a diagram illustrating a binarized image of an image of a subject in which there are a large number of non-uniform portions of makeup.

Here, FIGS. 29A and 29B illustrate binarized images obtained by generating a differential image, extracting a non-uniform portion P of makeup, and performing a binarization process on this differential image to emphasize the non-uniform portion P of the makeup with respect to the cheek portion of the madeup skin obtained by applying a foundation with different materials to a face F of the same subject. In FIG. 29A, the foundation in which the mass is unlikely to be generated has been applied, and in FIG. 29B, the foundation in which the mass is easily generated has been applied. Here, the non-uniform portion P of the makeup is displayed in a black point shape. As a result, it can be seen that there are a large number of non-uniform portions P of the makeup only near an eye in the binarized image of FIG. 29A, whereas the non-uniform portion P of the makeup is present throughout the evaluation region R9 in the binarized image of FIG. 29B. Therefore, it is suggested that the non-uniform portion P of the makeup is extracted with high accuracy through the above process.

Sensory evaluation was actually performed to evaluate the transparency of the madeup skins in FIGS. 29A and 29B, and the transparency of the madeup skin in FIG. 29A was evaluated to be higher than that of the madeup skin in FIG. 29B. Accordingly, the non-uniform portion P of the makeup provides a powder impression for the madeup skin, and it is considered that the transparency is evaluated to be low.

Therefore, the makeup non-uniformity calculation unit 62 calculates a degree of non-uniformity of the makeup from the binarized image from which the non-uniform portion P of the makeup has been extracted. The degree of the non-uniformity of the makeup may be calculated from, for example, a total area, an area proportion, and the number of the non-uniform portions in the evaluation region R9.

The makeup non-uniformity calculation unit 62 outputs the degree of the non-uniformity of the makeup in the evaluation region R9 as a makeup evaluation index to the overall index calculation unit 4. The degree of the non-uniformity of the makeup used as the makeup evaluation index is an evaluation index specific to the madeup skin exhibiting a decrease in the transparency due to the makeup, and can be used to evaluate the transparency from a different viewpoint from the skin evaluation index.

According to this embodiment, since the transparency is objectively evaluated according to a perception when the face F of the subject subjected to makeup is viewed as a whole based on the overall index in which the skin evaluation index and the makeup evaluation index are combined with each other, it is possible to obtain an evaluation result sufficiently coincident with the evaluation of the transparency through the sensory evaluation.

Further, the irregularity portion detected by the irregularity amount calculation unit 56 of Embodiment 5 is generated due to a wrinkle portion of the eye, but the wrinkle portion is not clearly present in everyone. Accordingly, even when the same makeup is applied, there is a person for which the irregularity portion is detected and a person for which the unevenness portion is not detected, leading to a difference in results of the evaluation of the transparency. In contrast, the non-uniform portion P of the makeup is generated due to a state of pores and skin grooves present in skins of a wide range of subjects, a cosmetic material, or the like. Accordingly, for the wide range of subjects, it is possible to evaluate the transparency of the madeup skin more accurately based on the non-uniformity of the makeup.

Figure 30:
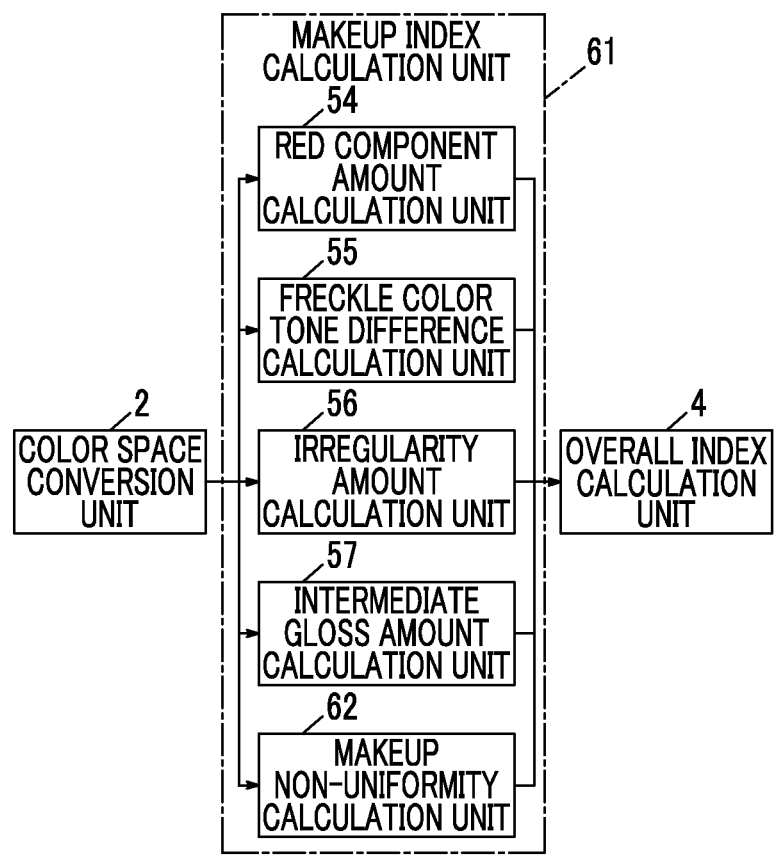
FIG. 30 is a block diagram illustrating a configuration of a makeup index calculation unit according to a modification example of Embodiment 6.

While in Embodiment 6 described above, the makeup non-uniformity calculation unit 62 has been arranged in place of the irregularity amount calculation unit 56 of Embodiment 5, the makeup index calculation unit 61 can be configured by newly adding the makeup non-uniformity calculation unit 62 to the makeup index calculation unit 53 of Embodiment 1, as illustrated in FIG. 30.

The evaluation of the transparency of the madeup skin as in Embodiments 5 and 6 may be executed by a transparency evaluation program recorded in a recording medium causing a computer including input means, a CPU, a memory, and the like to function. That is, by the transparency evaluation program recorded in the recording medium causing the computer to function, the image input unit acquires the captured image obtained by photographing the face of the subject subjected to makeup, and the CPU executes the preprocessing unit 1, the color space conversion unit 2, the index calculation unit 51, the overall index calculation unit 4, and the transparency evaluation unit 5 based on the acquired captured image to perform evaluation of the transparency for the subject subjected to makeup.

In Embodiment 5 described above, the skin index calculation unit 52 calculates the five skin evaluation indexes including the representative value of the luminance component, the representative value of the color component, the amount of generation of the negative factors, the amount of generation of the color unevenness, and the gradation characteristic, and the makeup index calculation unit 53 calculates the four makeup evaluation indexes including the amount of the red component, the color tone difference between the freckle portion and the surroundings thereof, the amount of the irregularity portion, and the amount of the intermediate gloss portion, but the present invention is not limited thereto. Further, in Embodiment 6 described above, the skin index calculation unit 52 calculates the five skin evaluation indexes including the representative value of the luminance component, the representative value of the color component, the amount of generation of the negative factors, the amount of generation of the color unevenness, and the gradation characteristic, and the makeup index calculation unit 61 calculates the four makeup evaluation indexes including the amount of the red component, the color tone difference between the freckle portion and the surroundings thereof, the degree of non-uniformity of the makeup, and the amount of the intermediate gloss portion, but the present invention is not limited thereto.

Specifically, by the skin index calculation unit 52 calculating at least one of the representative value of the luminance component, the representative value of the color component, and the amount of generation of the negative factors as a skin evaluation index, and the makeup evaluation calculation unit calculating the amount of the red component as a makeup evaluation index and combining the obtained skin evaluation index and the obtained makeup evaluation index with each other to calculate the overall index, it is possible to accurately evaluate the transparency of the madeup skin.

An embodiment in which the transparency of the madeup skin is actually evaluated using the transparency evaluation device of Embodiment 5 is shown.

Figure 31A:
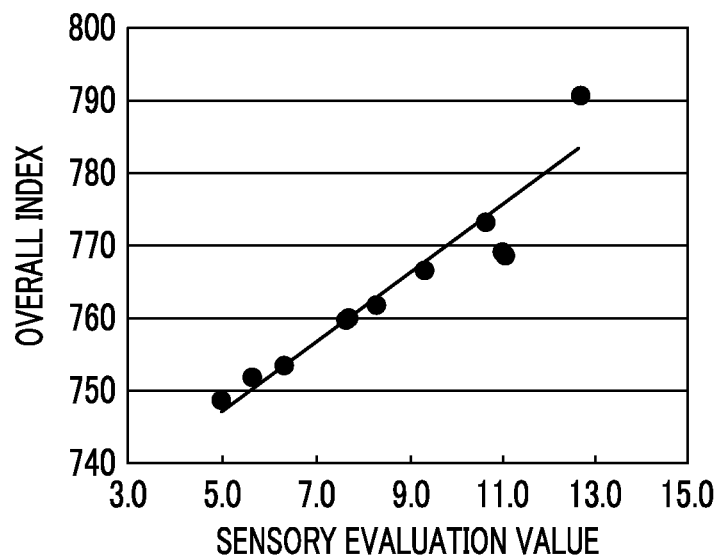
FIGS. 31A and 31B are diagrams illustrating an obtained correlation between the overall index and the sensory evaluation value for transparency of a madeup skin to which a liquid foundation has been applied.

In FIG. 31A, with respect to the face F of thirteen subjects to which the liquid foundation has been applied, the five skin evaluation indexes are combined with the three makeup evaluation indexes to calculate the overall index, sensory evaluation of the transparency is performed, and the overall index is plotted with respect to the sensory evaluation value obtained from the sensory evaluation.

Here, the overall evaluation value is calculated by combining the five skin evaluation indexes (the representative value L of the luminance component, the representative value C of the color component, the amount F of generation of the negative factor, the amount I of generation of the color unevenness, and the gradation characteristic K) with the three makeup evaluation indexes (an amount D of the red component, a color tone difference H between the freckle portion and surroundings thereof, and an amount B of the intermediate gloss portion) other than the amount of the irregularity portion. Specifically, overall index=A+10.5×L−2.6×C−28.1×F−0.9×I−1.0×K−(19.8×D−4.3×H+1.5×B). Further, A is a constant.

Figure 31B:
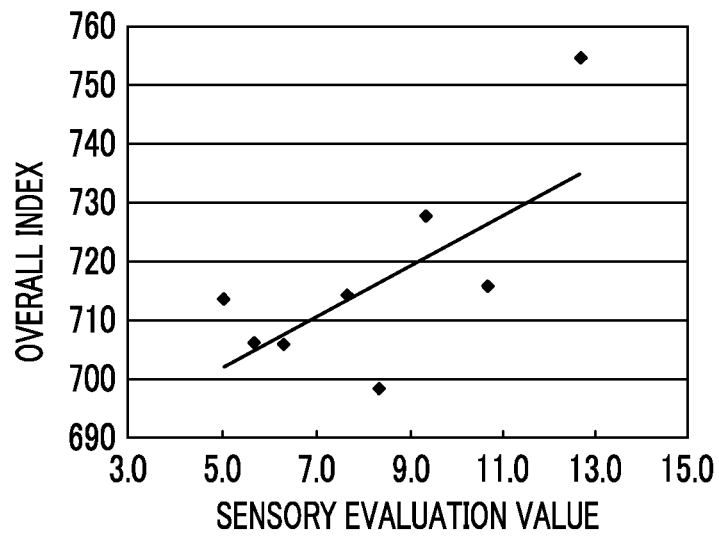

In FIG. 31B, with respect to the face F of nine subjects to which the liquid foundation has been applied, the five skin evaluation indexes are combined with one another to calculate the overall index, sensory evaluation of the transparency is performed, and the overall index is plotted with respect to the sensory evaluation value obtained from the sensory evaluation. Here, the overall evaluation value is calculated by combining five skin evaluation indexes including the representative value of the luminance component, the representative value of the color component, the amount of generation of the negative factors, an amount of the generation of the color unevenness, and the gradation characteristic with one another.

In FIGS. 31A and 31B, for the sensory evaluation value, the transparency is evaluated in 30 steps through sensory evaluation. No transparency is evaluated as the value is closer to 30.

In FIG. 31A, when the correlation between the overall index and the sensory evaluation value was obtained, the correlation coefficient $R^2$ was 0.90. On the other hand, in FIG. 31B, when the correlation between the overall index and the sensory evaluation value was obtained, the correlation coefficient $R^2$ was 0.46.

It can be seen from this that when the transparency of the madeup skin is evaluated from only the skin evaluation index, the transparency of the madeup skin cannot be accurately evaluated, and by combining the makeup evaluation index indicating the change in the transparency due to makeup with the skin evaluation index to evaluate the transparency of the madeup skin, an evaluation result sufficiently coincident with the sensory evaluation can be obtained, and the transparency of the madeup skin can be accurately evaluated.

Figure 32A:
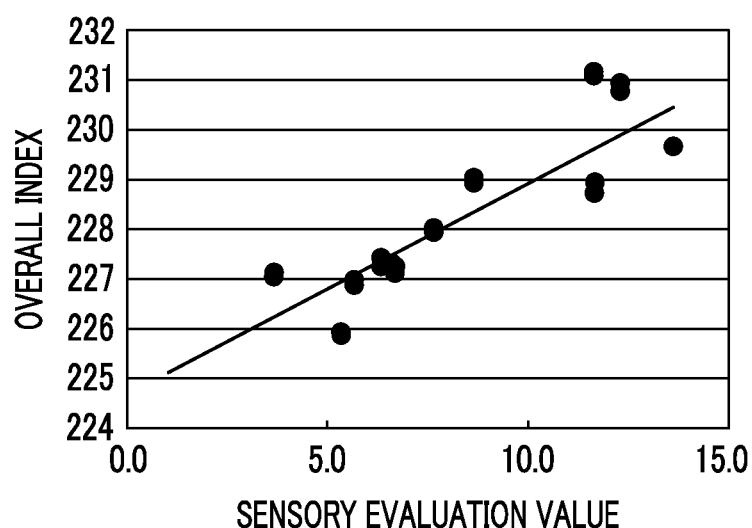
FIGS. 32A and 32B are diagrams illustrating an obtained correlation between the overall index and the sensory evaluation value for transparency of a madeup skin to which a powder foundation has been applied.

In FIG. 32A, with respect to the face F of fifteen subjects to which a powder foundation has been applied, the five skin evaluation indexes are combined with the three makeup evaluation indexes to calculate the overall index, sensory evaluation of the transparency is performed, and the overall index is plotted with respect to the sensory evaluation value obtained from the sensory evaluation.

Here, the overall evaluation value is calculated by combining the five skin evaluation indexes (the representative value L of the luminance component, the representative value C of the color component, the amount F of generation of the negative factor, the amount I of generation of the color unevenness, and the gradation characteristic K) with the three makeup evaluation indexes (an amount D of the red component, a color tone difference H between the freckle portion and surroundings thereof, and an amount W of the irregularity portion) other than an amount of the intermediate gloss portion. Specifically, overall index=A+3.79×L−1.67×C+0.25×F—0.18×I−1.9×K−(4.9×D−4.1×H−0.8×W). Further, A is a constant.

Figure 32B:
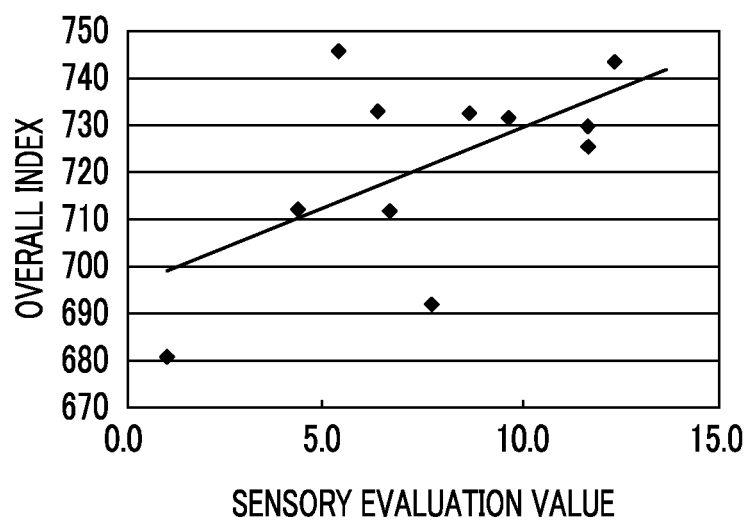

In FIG. 32B, with respect to the face F of eleven subjects to which the powder foundation has been applied, the five skin evaluation indexes are combined with one another to calculate the overall index, sensory evaluation of the transparency is performed, and the overall index is plotted with respect to the sensory evaluation value obtained from the sensory evaluation. Here, the overall evaluation value is calculated by combining five skill evaluation indexes including the representative value of the luminance component, the representative value of the color component, the amount of generation of the negative factors, an amount of the generation of the color unevenness, and the gradation characteristic with one another.

In FIGS. 32A and 32B, for the sensory evaluation value, the transparency is evaluated in 30 steps through sensory evaluation. No transparency is evaluated as the value is closer to 30.

In FIG. 32A, when the correlation between the overall index and the sensory evaluation value is obtained, the correlation coefficient $R^2$ was 0.70. On the other hand, in FIG. 32B, when the correlation between the overall index and the sensory evaluation value is obtained, the correlation coefficient $R^2$ was 0.33.

It can be seen from this that when the transparency of the madeup skin is evaluated from only the skin evaluation index, the transparency of the madeup skin cannot be accurately evaluated, and by combining the makeup evaluation index indicating the change in the transparency due to makeup with the skin evaluation index to evaluate the transparency of the madeup skin, an evaluation result sufficiently coincident with the sensory evaluation can be obtained, and the transparency of the madeup skin can be accurately evaluated.

Further, an embodiment in which the transparency of the madeup skin is evaluated using the transparency evaluation device according to Embodiment 6 illustrated in FIG. 27, and a result thereof is compared with a result of evaluating the transparency of the madeup skin using the transparency evaluation device according to Embodiment 5 is shown.

Figure 33A:
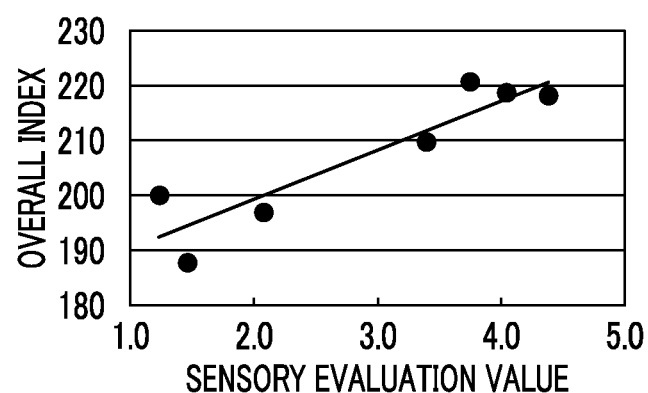
FIGS. 33A and 33B are diagrams illustrating an obtained correlation between the overall index and the sensory evaluation value for transparency of a madeup skin of a subject with clear wrinkle portions around eyes.
Figure 33B:
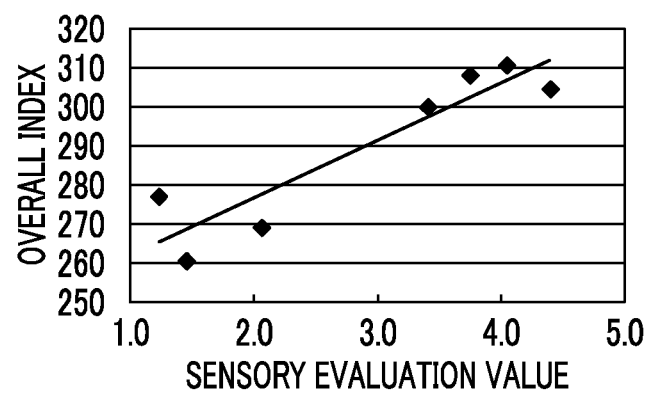

In FIGS. 33A and 33B, a foundation has been applied to a face F of a subject with a clear wrinkle portion around an eye, the skin evaluation index is combined with the makeup evaluation index using the transparency evaluation device of Embodiments 5 and 6 to calculate the overall index, sensory evaluation of the transparency is performed, and the overall index is plotted with respect to the sensory evaluation value obtained from the sensory evaluation.

Figure 34A:
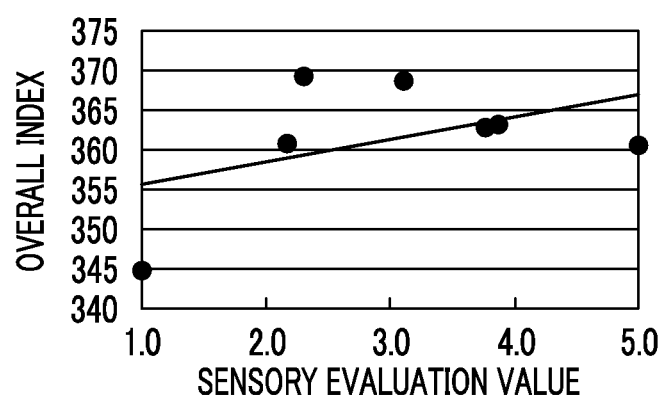
FIGS. 34A and 34B are diagrams illustrating an obtained correlation between the overall index and the sensory evaluation value for transparency of a madeup skin of a subject with an unclear wrinkle portion of eyes.
Figure 34B:
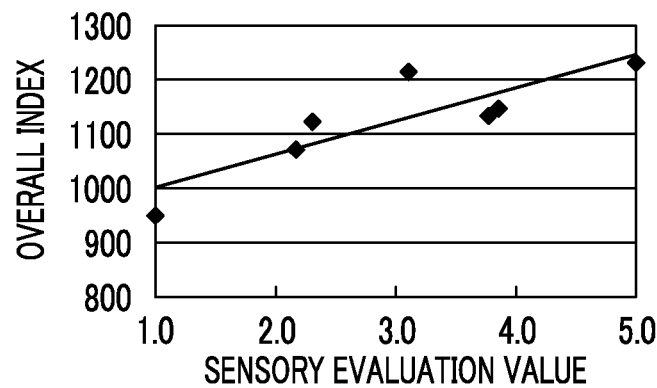

In FIGS. 34A and 34B, the same foundation as that in FIGS. 33A and 33B has been applied to a face F of a subject with an unclear wrinkle portion around an eye, the skin evaluation index is combined with the makeup evaluation index using the transparency evaluation device of Embodiments 5 and 6 to calculate the overall index, sensory evaluation of the transparency is performed, and the overall index is plotted with respect to the sensory evaluation value obtained from the sensory evaluation.

Here, in FIGS. 33A and 34A, using the transparency evaluation device of Embodiment 5, the five skin evaluation indexes (the representative value L of the luminance component, the representative value C of the color component, the amount F of generation of the negative factor, the amount I of generation of the color unevenness, and the gradation characteristic K) are combined with the three makeup evaluation indexes (an amount D of the red component, a color tone difference H between the freckle portion and surroundings thereof, and an amount W of the irregularity portion) to calculate the overall index. On the other hand, in FIGS. 33B and 34B, using the transparency evaluation device of Embodiment 6, the five skin evaluation indexes (the representative value L of the luminance component, the representative value C of the color component, the amount F of generation of the negative factor, the amount I of generation of the color unevenness, and the gradation characteristic K) are combined with the three makeup evaluation indexes (the amount D of the red component, the color tone difference H between the freckle portion and surroundings thereof, and non-uniformity P of the makeup) to calculate the overall index.

In FIGS. 33A and 33B and FIGS. 34A and 34B, for the sensory evaluation value, the transparency is evaluated in 5 steps through sensory evaluation. Transparency is evaluated to be high as the value is closer to 5.

In FIGS. 33A and 33B, when the correlation between the overall index and the sensory evaluation value is obtained, the correlation coefficient $R^2$ of FIG. 33A was 0.83, and the correlation coefficient $R^2$ of FIG. 33B was 0.85. On the other hand, in FIGS. 34A and 34B, when the correlation between the overall index and the sensory evaluation value is obtained, the correlation coefficient $R^2$ of FIG. 34A was 0.12, and the correlation coefficient $R^2$ of FIG. 34B was 0.80.

It can be seen from the above that when the transparency of the madeup skin is evaluated based on the amount of the irregularity portion, an evaluation result showing a high correlation with the sensory evaluation is obtained as illustrated in FIG. 33A with respect to the subject with a clear irregularity portion, whereas the correlation with the sensory evaluation is low as illustrated in FIG. 34A, and an evaluation result varies according to subjects with respect to the subject with an unclear irregularity portion. On the other hand, when the transparency of the madeup skin is evaluated based on the non-uniformity of the makeup, it is suggested that an evaluation result showing a high correlation with the sensory evaluation is obtained as illustrated in FIGS. 33B and 34B with respect to any subject, and an accurate evaluation result varying less according to subjects is obtained.

While the evaluation of transparency has been performed on the madeup skin to which the foundation has been applied in the above embodiment, the madeup skin may be any skin subjected to makeup and the present invention is not limited thereto. For example, the evaluation of transparency may be similarly performed on a madeup skin to which a skin correction agent such as a masking agent (for example, $TiO_2$) and a pigment and, specifically, a BB cream, a CC cream, a cosmetic foundation, a sunscreen, or the like is applied.

EXPLANATION OF REFERENCES

1: preprocessing unit
1a: image input unit
2: color space conversion unit
3 and 51: index calculation unit
4: overall index calculation unit
5: transparency evaluation unit
6: display unit
7: control unit
8: operating unit
9: luminance and color calculation unit
10: gradation characteristic calculation unit
21 and 22: negative factor calculation unit
31 and 41: color unevenness calculation unit
52: skin index calculation unit
53 and 61: makeup index calculation unit
54: red component amount calculation unit
55: freckle color tone difference calculation unit
56: irregularity amount calculation unit
57: intermediate gloss amount calculation unit
62: makeup non-uniformity calculation unit
F: face
C: camera
R1, R2, and R5 to R9: evaluation region
M: contour line
G: L* component contour line distribution image
S1 and S2: contour line spacing
D: red component L: low luminance portion
P: unevenness portion

What is claimed is:

1. A transparency evaluation device comprising:
   an image input processor that inputs a captured image obtained by photographing a skin of a subject;
   a skin index calculation processor that calculates at least one of a representative value of a luminance component in the captured image, a representative value of a color component in the captured image, and an amount of generation of negative factors in which a value of the luminance component or a value of the color component in the captured image changes locally, as a first skin evaluation index, obtains at least one of an intensity distribution of the luminance component and an intensity distribution of the color component in the captured image, and calculates at least one of smoothness of a change in the luminance component and smoothness of a change in the color component as a second skin evaluation index based on the obtained intensity distributions;
   an overall index calculation processor that combines a plurality of evaluation indexes including the first skin evaluation index and the second skin evaluation index calculated by the skin index calculation processor with one another to calculate an overall index for transparency of the skin; and
   a transparency evaluation processor that evaluates transparency of the skin of the subject based on the overall index calculated by the overall index calculation processor.

2. The transparency evaluation device according to claim 1,
   wherein the skin index calculation processor partitions the captured image according to the value of the luminance component and the value of the color component using a plurality of contour lines set stepwise with uniform intensity spacings in order to obtain the intensity distribution of the luminance component and the intensity distribution of the color component in the captured image.

3. The transparency evaluation device according to claim 2,
   wherein the skin index calculation processor obtains respective spacings of the plurality of contour lines adjacent to each other, and calculates the second skin evaluation index based on uniformity of the obtained spacings of the plurality of contour lines.

4. The transparency evaluation device according to claim 2,
   wherein the skin index calculation processor calculates the second skin evaluation index based on the number of the plurality of contour lines partitioning the captured image.

5. The transparency evaluation device according to claim 1,
   wherein the skin index calculation processor sets the evaluation region for calculating the second skin evaluation index so that a linear connection from a cheek portion of the face of the subject to an outline portion of the face is made.

6. The transparency evaluation device according to claim 1,
   wherein the skin index calculation processor calculates an average value of the luminance component in the captured image as a representative value of the luminance component, and calculates an average value of the color component in the captured image as a representative value of the color component.

7. The transparency evaluation device according to claim 1,
   wherein the skin index calculation processor calculates the number, a total area, or an area proportion of the negative factors detected from the captured image as an amount of generation of the negative factors.

8. The transparency evaluation device according to claim 1,
   wherein the skin index calculation processor detects a portion in which the value of the luminance component or the value of the color component in the captured image changes locally and that is larger than the negative factors as color unevenness, and calculates an amount of generation of the detected color unevenness as a third skin evaluation index, and
   the overall index calculation processor combines a plurality of evaluation indexes further including the third skin evaluation index with one another to calculate the overall index.

9. The transparency evaluation device according to claim 8,
   wherein the skin index calculation processor calculates a total area, an area proportion, or the number of instances of color unevenness detected from the captured image as an amount of generation of the color unevenness.

10. A transparency evaluation method comprising:
    inputting a captured image obtained by photographing a skin of a subject;
    calculating at least one of a representative value of a luminance component in the captured image, a representative value of a color component in the captured image, and an amount of generation of negative factors in which a value of the luminance component or a value of the color component in the captured image changes locally, as a first skin evaluation index, obtaining at least one of an intensity distribution of the luminance component and an intensity distribution of the color component in the captured image, and calculating at least one of smoothness of a change in the luminance component and smoothness of a change in the color component as a second skin evaluation index based on the obtained intensity distributions;
    combining a plurality of evaluation indexes including the first skin evaluation index and the second skin evaluation index that have been calculated with one another to calculate an overall index for transparency of the skin; and
    evaluating transparency of the skin of the subject based on the calculated overall index.

11. A non-transitory computer-readable medium storing a transparency evaluation program for causing a computer to execute the steps of:
    acquiring a captured image obtained by photographing a skin of a subject;
    calculating at least one of a representative value of a luminance component in the captured image, a representative value of a color component in the captured image, and an amount of generation of negative factors in which a value of the luminance component or a value of the color component in the captured image changes locally, as a first skin evaluation index, obtaining at least one of an intensity distribution of the luminance component and an intensity distribution of the color component in the captured image, and calculating at least one of smoothness of a change in the luminance component and smoothness of a change in the color component as a second skin evaluation index based on the obtained intensity distributions;

combining a plurality of evaluation indexes including the first skin evaluation index and the second skin evaluation index that have been calculated with one another to calculate an overall index for transparency of the skin; and evaluating transparency of the skin of the subject based on the calculated overall index.

* * * * *